(12) United States Patent
Sato et al.

(10) Patent No.: US 10,984,197 B2
(45) Date of Patent: Apr. 20, 2021

(54) INFORMATION TRANSMISSION DEVICE AND NON-TRANSITORY COMPUTER READABLE MEDIUM

(71) Applicant: FUJI XEROX CO., LTD., Tokyo (JP)

(72) Inventors: Masahiro Sato, Kanagawa (JP); Kengo Tokuchi, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 92 days.

(21) Appl. No.: 15/984,424

(22) Filed: May 21, 2018

(65) Prior Publication Data
US 2019/0179899 A1  Jun. 13, 2019

(30) Foreign Application Priority Data
Dec. 8, 2017  (JP) ............................. JP2017-236152

(51) Int. Cl.
| | |
|---|---|
| *G06F 40/30* | (2020.01) |
| *A61B 5/00* | (2006.01) |
| *A61B 5/117* | (2016.01) |
| *G16H 50/20* | (2018.01) |
| *G16H 10/20* | (2018.01) |

(52) U.S. Cl.
CPC ............ *G06F 40/30* (2020.01); *A61B 5/0022* (2013.01); *A61B 5/4803* (2013.01); *A61B 5/486* (2013.01); *A61B 5/6843* (2013.01); *A61B 5/7282* (2013.01); *A61B 5/7465* (2013.01); *G16H 50/20* (2018.01); *A61B 5/117* (2013.01)

(58) Field of Classification Search
CPC ..... G06F 17/2785; G16H 50/20; A61B 5/117; A61B 5/486; A61B 5/4803; A61B 5/6843
See application file for complete search history.

(56) References Cited

U.S. PATENT DOCUMENTS

| | | | | |
|---|---|---|---|---|
| 7,260,231 B1 * | 8/2007 | Wedge | ...................... | H04R 3/00 |
| | | | | 381/310 |
| 8,715,179 B2 * | 5/2014 | Price | ........................ | A61B 5/01 |
| | | | | 600/300 |
| 9,138,186 B2 * | 9/2015 | Price | .................. | A61B 5/02055 |
| 10,242,501 B1 * | 3/2019 | Pusch | .................... | H04N 19/43 |
| 10,490,309 B1 * | 11/2019 | McNair | .................. | G16H 10/60 |
| 2001/0029322 A1 * | 10/2001 | Iliff | ........................ | G16H 10/60 |
| | | | | 600/300 |

(Continued)

FOREIGN PATENT DOCUMENTS

| | | |
|---|---|---|
| CN | 106484093 | 3/2017 |
| JP | 2011160260 | 8/2011 |
| JP | 2012054892 | 3/2012 |

OTHER PUBLICATIONS

"Office Action of China Counterpart Application", dated Jan. 28, 2021, with English translation thereof, p. 1-p. 29.

*Primary Examiner* — Daniel C Washburn
*Assistant Examiner* — Oluwadamilola M Ogunbiyi
(74) *Attorney, Agent, or Firm* — JCIPRNET

(57) ABSTRACT

An information transmission device includes: a determining unit that determines a situation of an interlocutor who interacts with a user; and a transmission unit that transmits, to the user, information to be provided according to the situation of the interlocutor determined by the determining unit. In a further modification of the invention, the determining unit may determine a situation related to a body or conversation of the interlocutor as the situation of the interlocutor.

21 Claims, 17 Drawing Sheets

(56) References Cited

U.S. PATENT DOCUMENTS

| | | | | |
|---|---|---|---|---|
| 2002/0002465 | A1* | 1/2002 | Maes | G10L 15/065 704/275 |
| 2003/0073887 | A1* | 4/2003 | Iliff | G16H 50/20 600/300 |
| 2005/0278207 | A1* | 12/2005 | Ronnewinkel | G06Q 30/02 705/326 |
| 2008/0040780 | A1* | 2/2008 | Reinhold | H04L 63/30 726/5 |
| 2010/0082363 | A1* | 4/2010 | Warner | G16H 40/20 705/2 |
| 2013/0116578 | A1* | 5/2013 | An | A61B 5/4842 600/484 |
| 2013/0138457 | A1* | 5/2013 | Ragusa | G06Q 10/10 705/3 |
| 2015/0164436 | A1* | 6/2015 | Maron | A61B 17/00234 340/540 |
| 2015/0221247 | A1* | 8/2015 | Herger | G02B 27/017 345/8 |
| 2016/0022193 | A1* | 1/2016 | Rau | A61B 5/165 600/301 |
| 2016/0155256 | A1* | 6/2016 | Makofsky | G06K 9/00281 345/581 |
| 2016/0180038 | A1* | 6/2016 | Clark | G06F 16/3334 706/12 |
| 2016/0212466 | A1* | 7/2016 | Nauseef | H04N 21/2668 |
| 2016/0232328 | A1* | 8/2016 | Sklar | G16H 10/20 |
| 2017/0060839 | A1* | 3/2017 | Kawamura | G10L 25/63 |
| 2017/0255403 | A1* | 9/2017 | Sharon | G11C 11/5642 |
| 2017/0281097 | A1* | 10/2017 | Thakur | G16H 40/63 |
| 2017/0296303 | A1* | 10/2017 | Tod | A61C 7/002 |
| 2018/0061399 | A1* | 3/2018 | Rose | G10L 15/22 |
| 2018/0144745 | A1* | 5/2018 | Park | H04N 21/4828 |
| 2018/0204572 | A1* | 7/2018 | Manabe | G06K 9/00845 |
| 2018/0293528 | A1* | 10/2018 | Bostick | G06Q 10/06316 |
| 2019/0050239 | A1* | 2/2019 | Caldwell | G06Q 30/016 |
| 2019/0122160 | A1* | 4/2019 | Kolandaiswamy | H04L 63/108 |
| 2019/0179959 | A1* | 6/2019 | Dechu | G06F 16/68 |
| 2019/0192009 | A1* | 6/2019 | Reifman | A61B 5/024 |
| 2019/0254882 | A1* | 8/2019 | Trennepohl | A61F 13/15699 |
| 2020/0118164 | A1* | 4/2020 | DeFrank | G06Q 30/0269 |
| 2020/0129120 | A1* | 4/2020 | Adachi | G16H 20/10 |

* cited by examiner

FIG.1A

DOCTOR: DO YOU DRINK ALCOHOL?
PATIENT: YES
DOCTOR: HOW OFTEN AND HOW MUCH?
PATENT : ABOUT 0.4 PINTS OF SAKE EVERY NIGHT

FIG.1B

SALESMAN : MARRIED OR UNMARRIED?
CUSTOMER: UNMARRIED
SALESMAN : HOW MUCH SPACE DO YOU CURRENTLY HAVE FOR INSTALLING A REFRIGRATOR?
CUSTOMER: ABOUT XX?
SALESMAN : HOW MUCH IS YOUR BUDGET?
CUSTOMER: ABOUT YY YEN

FIG.1C

MAINTENANCE MAN: HAVE SHEETS BEEN FED FROM THOSE LOADED IN THE CASSETTE?
CUSTOMER : YES

INFORMATION TRANSMISSION DEVICE AND NON-TRANSITORY COMPUTER READABLE MEDIUM

CROSS-REFERENCE TO RELATED APPLICATIONS

This application is based on and claims priority under 35 USC 119 from Japanese Patent Application No. 2017-236152 filed Dec. 8, 2017.

BACKGROUND

(i) Technical Field

The present invention relates to an information transmission device and a non-transitory computer readable medium.

(ii) Related Art

In this regard, a configuration may be used which merely transmits, to a user, information related to the degree of emotional feelings of an interlocutor who interacts with the user. In this case, it is not possible to transmit, to the user, information to be provided according to the situation of the interlocutor who interacts with the user.

SUMMARY

According to an aspect of the invention, an information transmission device includes: a determining unit that determines a situation of an interlocutor who interacts with a user; and a transmission unit that transmits, to the user, information to be provided according to the situation of the interlocutor determined by the determining unit.

BRIEF DESCRIPTION OF THE DRAWINGS

Exemplary embodiments of the present invention will be described in detail based on the following figures, wherein:

FIGS. 1A to 1C are views illustrating an example of contents of conversation in respective situations;

DETAILED DESCRIPTION

Figure 2:
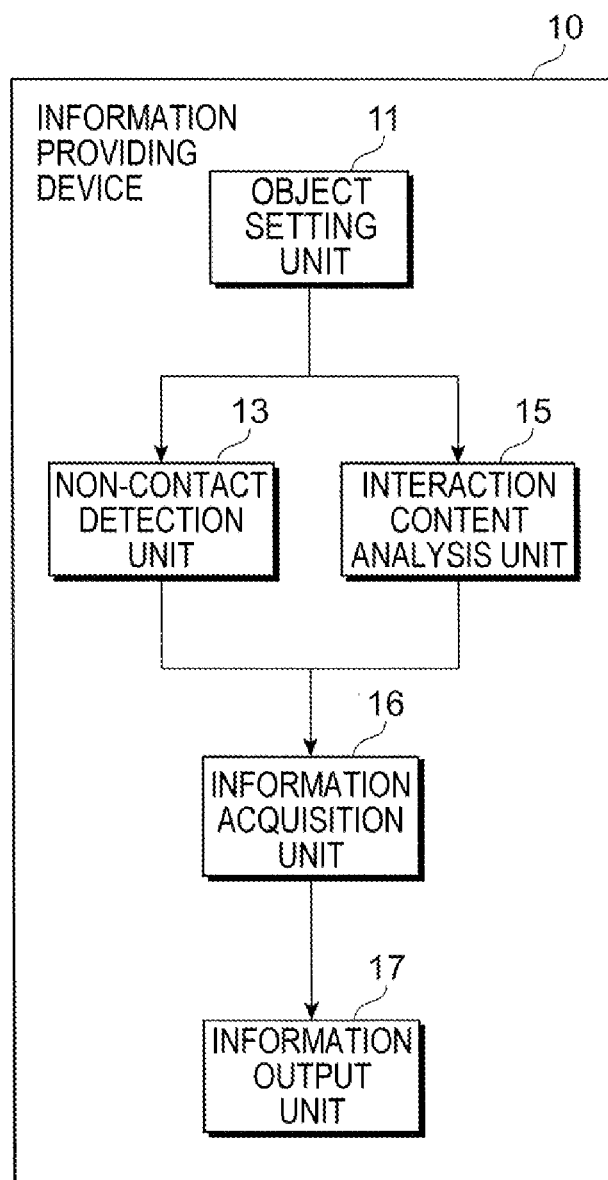
FIG. 2 is a block diagram illustrating a functional configuration example of an information providing device according to a first exemplary embodiment of the invention.

Hereinafter, exemplary embodiments of the invention will be described with reference to the accompanying drawings.

The exemplary embodiments provide a device capable of determining the situation of an interlocutor (partner user) who interacts with a user (operating user) and transmitting, to the operating user, information to be provided according to the determined situation of the partner user (hereinafter referred to as the "information to be provided"). In the following description, conversation in two situations will be provided as the interaction between the operating user and the partner user, although the invention is not limited in this respect. The first situation is a situation where it is effective to reflect the physical condition of the partner user in the information to be provided. For example, there is a situation where a doctor consults a patient with a certain symptom. The second situation is a situation where it is effective to reflect a change in the physical condition of the partner user in the information to be provided. For example, there are a situation where a salesman talks with a customer who is planning to purchase a certain product and a situation where a maintenance man talks with a customer who is complaining about a defect of a product.

FIGS. 1A to 1C are views illustrating examples of contents of conversation in these situations.

FIG. 1A is an example of conversation in a situation where a doctor consults a patient with a certain symptom as mentioned above. Here, in response to a question "How often and how much?" asked by the doctor, the patient answers "About 0.4 pints of Sake every night". In this case, when the physical condition of the patient is such that the blood pressure and the pulse rate are high, the information to be provided according to the physical condition of the patient may be a recommendation to refrain from drinking alcohol and to receive a detailed examination, which will be provided to the doctor.

FIG. 1B is an example of conversation in a situation where a salesman talks with a customer who is planning to purchase a certain product (for example, a refrigerator). In response to a question "How much space do you currently have for installing a refrigerator?" asked by the salesman, the customer answers "About XX?". Then, in response to a question "How much is your budget?" asked by the salesman, the customer answers "About YY Yen". At the time of these answers, it is assumed that a change in the customer's physical condition is large. Regarding the installation space, there is a possibility that the change in the physical condition is large because of the ambiguous answer of "About XX?", and thus, it is unclear whether the answer is in line with the actual intention of the customer. However, regarding the budget, since the change in the customer's physical condition is large despite the clear answer "About YY Yen", there is a possibility that the answer presents a high budget contrary to the actual intention. Therefore, the information to be provided according to the change in the physical condition of the customer may be a recommendation to advance dialogue toward keeping the budget low, which will be provided to the salesman.

FIG. 1C is an example of conversation in a situation where a maintenance man talks with a customer who is complaining about a defect (for example, sheet jam) of a certain product (for example, a printer). Here, the customer answers "Yes" to a question "Have sheets been fed from those loaded in the cassette?" asked by the maintenance man. At the time of this answer, when there is a large change in the customer's physical condition, the answer may be contrary to the fact. Therefore, the information to be provided according to the change in the physical condition of the customer may be a recommendation to check whether or not sheets have been fed manually, whether or not sheets have absorbed moisture, or the like, which will be provided to the maintenance man.

Hereinafter, a device that provides such information as mentioned above will be referred to as an information providing device, and information providing devices according to the exemplary embodiments will be described in detail. A description will be given in which the body-related situation of the partner user and the conversation-related situation of the partner user are used as examples of the situation of the partner user.

First Exemplary Embodiment

FIG. 2 is a block diagram illustrating a functional configuration example of an information providing device 10 according to a first exemplary embodiment. As illustrated, the information providing device 10 according to the first exemplary embodiment includes an object setting unit 11, a non-contact detection unit 13, an interaction content analysis unit 15, an information acquisition unit 16, and an information output unit 17.

The object setting unit 11 sets an object for which information will be provided. Here, the object to be set may be a broad category such as consultation, sales, or maintenance. However, in the case described below, a more specific category, such as the symptom of a patient for consultation, a product for sales, or a defect of a product for maintenance, is set as the object.

For consultation, for example, when a doctor who is an operating user selects a certain symptom from a list of symptoms prepared in advance, the object setting unit 11 may set the selected symptom as the object. Alternatively, the object setting unit 11 may expect a symptom by analyzing an interview sheet filled in advance by a patient, and set the expected symptom as the object.

For sales, for example, when a salesman who is an operating user selects a certain product from a list of products prepared in advance, the object setting unit 11 may set the selected product as the object. Alternatively, the object setting unit 11 may expect a product to be purchased by analyzing conversation made at the time when a customer visits a store, and set the expected product as the object.

For maintenance, for example, when a maintenance man who is an operating user selects a certain defect from a list of defects prepared in advance, the object setting unit 11 may set the selected defect as the object. Alternatively, the object setting unit 11 may estimate a defect by analyzing the condition of the maintenance target product, and set the estimated defect as the object.

In the exemplary embodiment, the object setting unit 11 is provided as an example of a specifying unit that specifies the object of determining a situation of an interlocutor.

The non-contact detection unit 13, which is connected to a non-contact sensor (not illustrated) capable of measuring biometric information without directly contacting with the body of a partner user, acquires the biometric information detected by the non-contact sensor, and provides, as detected information, the biometric information or a calculated temporal change in the biometric information. The non-contact sensor used here may be a non-contact sensor capable of measuring, for example, body temperature, pulsation, blood flow state, or the like. For consultation, the non-contact detection unit 13 determines the body temperature, pulsation, blood flow state, or the like of the partner user as detected information. For sales or maintenance, the non-contact detection unit 13 determines a calculated temporal change in the body temperature, pulsation, blood flow state, or the like of the partner user as detected information. In the exemplary embodiment, the non-contact sensor is used as an example of a non-contact detector that detects the physical condition of the interlocutor without contacting with the body of the interlocutor, and the non-contact detection unit 13 is provided as an example of a determining unit that determines the physical condition of the interlocutor or a change in the condition using the non-contact detector.

The interaction content analysis unit 15 analyzes the contents of an answer to a question that the operating user has made to the partner user, and extracts a keyword matching the object set by the object setting unit 11 from the contents of the answer. Further, in the first situation, a word related to the keyword is further extracted from the contents of the answer. In addition, when a word indicating affirmation or negation for the question such as "Yes" or "No" is present in the answer, the interaction content analysis unit 15 also analyzes the question in order to determine what the word indicates affirmation or negation for.

For consultation, for example, the doctor asks the patient with the symptom, which is set as the object, a question on a matter affecting the symptom, and the patient answers the question. Then, the interaction content analysis unit 15 records and analyzes the contents of the answer and extracts a keyword associated with the symptom. Such a keyword may be a keyword related to a lifestyle habit, such as "alcohol", "tobacco", or the like. In addition, the interaction content analysis unit 15 holds an object-specific dictionary in which, for each symptom, keywords are linked to keyword-related items. When the keyword is "alcohol" or "tobacco", the related item is, for example, frequency or quantity. Thus, the interaction content analysis unit 15 extracts a related word such as "once per x days", "xx pints" or the like, which indicates specific contents of the related item linked to the keyword in the object-specific dictionary, from portions around the keyword in the contents of the answer. The keyword and the related word extracted in this way are hereinafter referred to as "extracted information".

For sales, for example, the salesman asks the customer, who is planning to purchase a product set as the object, a question on the background and circumstances under the plan to purchase the product, the interest and preference for the product, or the like, and the customer answers the question. Then, the interaction content analysis unit 15 records and analyzes the contents of the answer and extracts a keyword associated with the product. Such a keyword includes, for example, a keyword related to an installation space when the product is large, or a keyword related to a budget when the product is expensive.

For maintenance, for example, the maintenance man asks the customer, who is complaining about a defect of a product set as the object, a question on the situation of use of the product at the time of occurrence of the defect, the situation of the defect, or the like, and the customer answers the question. Then, the interaction content analysis unit 15 records and analyzes the contents of the answer and extracts a keyword associated with the defect. Such a keyword includes, for example, a keyword related to the sheet feeding method, the sheet storage conditions, or the like when the defect is related to sheet jam in a printer.

In the exemplary embodiment, the interaction content analysis unit 15 is provided as an example of a determining unit that determines the contents of the answer of the interlocutor to the question of the user.

The information acquisition unit 16 collates the biometric information or a change in the biometric information, which is information detected by the non-contact detection unit 13, with the extracted information or the keyword, which is extracted by the interaction content analysis unit 15, to acquire information to be provided.

In the first situation, the information acquisition unit 16 determines whether or not information to be provided is registered in association with the extracted information and the biometric information in an object-specific database. When it is determined that information to be provided is registered, the information acquisition unit 16 acquires the information to be provided. For consultation, for example, when information to be provided, such as a lifestyle habit having adverse effect on the symptom or the medicine that will be prescribed for the symptom, is registered in association with the extracted information and the biometric information in a database for each symptom, the information acquisition unit 16 acquires the information to be provided.

In the second situation, when the change in the biometric information is large at the time of appearance of the keyword in the contents of an answer, the information acquisition unit 16 acquires information to be provided according to the keyword. For sales and maintenance, for example, the information acquisition unit 16 may acquire, as the information to be provided, a keyword appearing when the change in the biometric information is significant.

The information output unit 17 outputs, to an operating user, the information to be provided, which is acquired by the information acquisition unit 16. In the case described below, the information to be provided is output by voice through a sound output unit 97 (see FIG. 17), although the invention is not limited in this respect. In the exemplary embodiment, the information output unit 17 is provided as an example of the transmission unit that transmits, to the user, the information to be provided according to the situation of the interlocutor.

In the first exemplary embodiment, the non-contact detection unit 13 and the interaction content analysis unit 15 are provided as an example of the determining unit that determines the contents of an answer of the interlocutor to a question of the user. However, only one of them may be provided. Further, when the information providing device 10 is a device having only a single object for providing information, the object setting unit 11 may not be provided.

Figure 3:
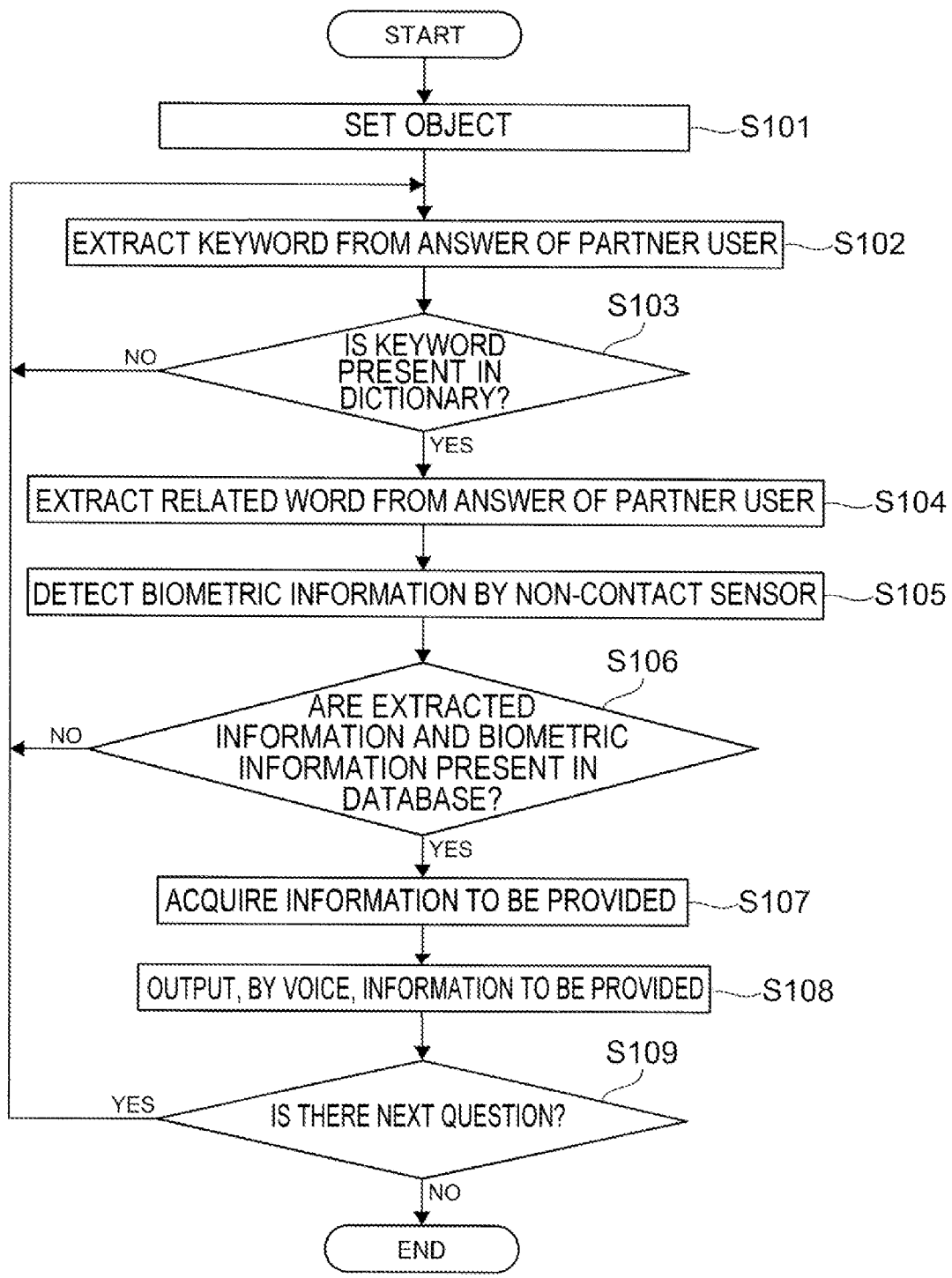
FIG. 3 is a flowchart illustrating an operation example of the information providing device according to the first exemplary embodiment of the invention in a first situation.

FIG. 3 is a flowchart illustrating an operation example of the information providing device 10 in the first situation according to the first exemplary embodiment.

As illustrated, in the information providing device 10, first, the object setting unit 11 sets the object of providing information (step 101).

In this state, when an operating user asks the partner user a question and the partner user answers the question, the interaction content analysis unit 15 extracts a keyword from the answer (step 102). Then, it is determined whether or not the extracted keyword is registered in the object-specific dictionary (step 103).

When it is determined that the keyword is registered in the object-specific dictionary, the interaction content analysis unit 15 extracts a related word from the answer (step 104). Specifically, a related item registered in the object-specific dictionary in association with the keyword is acquired and a related word indicating the specific contents of the related item is extracted from the answer.

Meanwhile, the non-contact detection unit 13 uses the non-contact sensor to detect the biometric information of the partner user (step 105).

Then, the information acquisition unit 16 determines whether or not the pair of the information extracted in steps 102 and 104 and the biometric information detected in step 105 is registered in the database (step 106).

When it is determined that the pair of the extracted information and the biometric information is registered in the database, the information acquisition unit 16 acquires the information to be provided, which is registered in the database in association with this pair (step 107).

Next, the information output unit 17 outputs the information acquired in step 107 to the operating user by voice (step 108).

Thereafter, the interaction content analysis unit 15 determines whether or not the operating user is asking the partner user the next question (step 109). In addition, even when it is determined in step 103 that the keyword is not registered in the object-specific dictionary or even when it is determined in step 106 that the pair of the extracted information and the biometric information is not registered in the database, the interaction content analysis unit 15 determines whether or not the operating user is asking the partner user the next question (step 109). When it is determined that the operating user is asking the partner user the next question, the information providing device 10 returns the process to step 102 to repeat the subsequent steps. On the other hand, when it is determined that the operating user is not asking the partner user the next question, the information providing device 10 ends the process.

Figure 4:
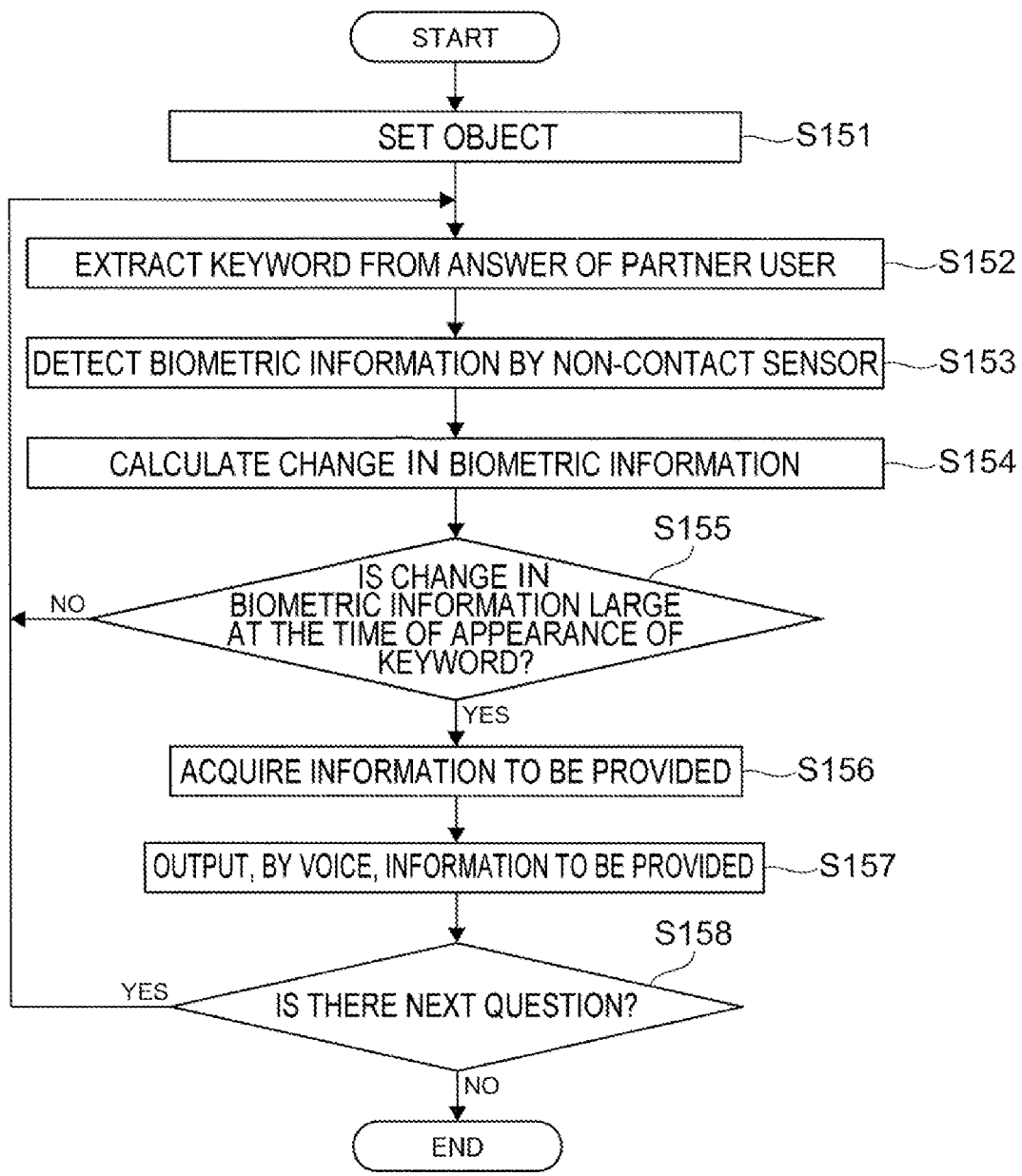
FIG. 4 is a flowchart illustrating an operation example of the information providing device according to the first exemplary embodiment of the invention in a second situation.

FIG. 4 is a flowchart illustrating an operation example of the information providing device 10 in the second situation in the first exemplary embodiment.

As illustrated, in the information providing device 10, first, the object setting unit 11 sets the object of providing information (step 151).

In this state, when the operating user asks the partner user a question and the partner user answers the question, the interaction content analysis unit 15 extracts a keyword from the answer (step 152).

Meanwhile, the non-contact detection unit 13 uses the non-contact sensor to detect the biometric information of the partner user (step 153). Then, the non-contact detection unit 13 calculates a change in the detected biometric information (step 154).

Then, the information acquisition unit 16 determines whether or not the change in the biometric information calculated in step 154 is large at the time of appearance of the keyword extracted in step 152 (step 155). Specifically, the information acquisition unit 16 determines whether or not the change in the biometric information calculated in step 154 is larger than a predetermined threshold value.

When it is determined that the change in the biometric information is large at the time of appearance of the keyword, the information acquisition unit 16 acquires information to be provided according to this keyword (step 156).

Next, the information output unit 17 outputs, to the operating user by voice, the information to be provided (step 157), which is acquired in step 156.

Thereafter, the interaction content analysis unit 15 determines whether or not the operating user is asking the partner user the next question (step 158). Even when it is determined in step 155 that the change in the biometric information is not large at the time of appearance of the keyword, the interaction content analysis unit 15 determines whether or not the operating user is asking the partner user the next question (step 158). When it is determined that the operating user is asking the partner user the next question, the information providing device 10 returns the process to step 152 to repeat the subsequent steps. On the other hand, when it is determined that the operating user is not asking the partner user the next question, the information providing device 10 ends the process.

Second Exemplary Embodiment

Figure 5:
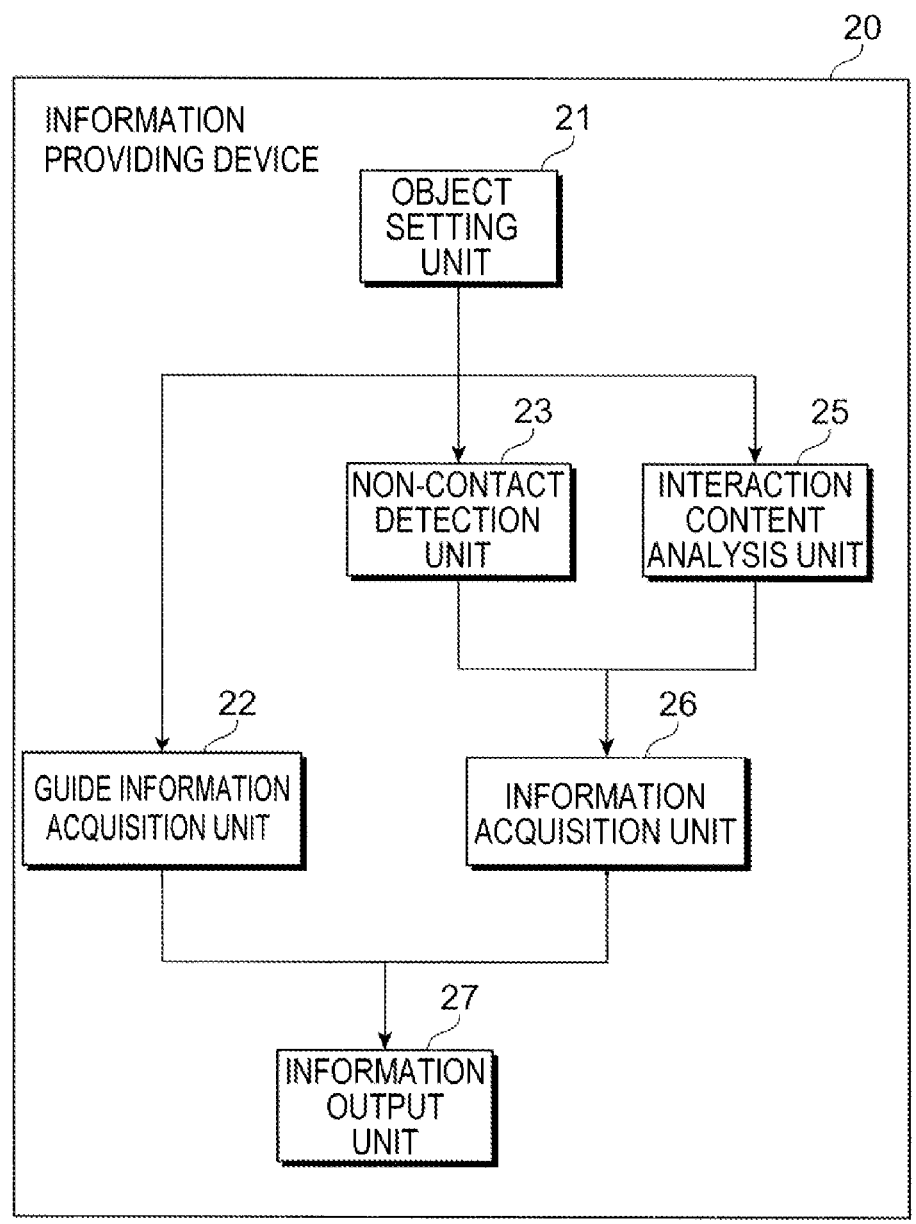
FIG. 5 is a block diagram illustrating a functional configuration example of an information providing device according to a second exemplary embodiment of the invention.

FIG. 5 is a block diagram illustrating a functional configuration example of an information providing device 20 according to a second exemplary embodiment. As illustrated, the information providing device 20 according to the second exemplary embodiment includes an object setting unit 21, a guide information acquisition unit 22, a non-contact detection unit 23, an interaction content analysis unit 25, an information acquisition unit 26 and an information output unit 27.

The object setting unit 21, the non-contact detection unit 23, the interaction content analysis unit 25 and the information acquisition unit 26 correspond respectively to the object setting unit 11, the non-contact detection unit 13, the interaction content analysis unit 15 and the information acquisition unit 16 in the first exemplary embodiment and therefore, descriptions thereof will not be repeated.

The guide information acquisition unit 22 acquires guide information that guides the flow of a question according to the object set by the object setting unit 21.

The information output unit 27 outputs, to an operating user, the guide information, which is acquired by the guide information acquisition unit 22, and the information to be provided, which is acquired by the information acquisition unit 26. In the case described below, the information to be provided is output by voice through a sound output unit 97 (see FIG. 17), although the invention is not limited in this respect. In the exemplary embodiment, the guide information is used as an example of instruction information instructing a procedure for determining the situation of the interlocutor. In addition, the information output unit 27 is provided as an example of a transmission unit that transmits, to the user, the information to be provided according to the situation of the interlocutor, and as an example of a transmission unit that transmits the instruction information to the user.

In the second exemplary embodiment, the non-contact detection unit 23 and the interaction content analysis unit 25 are provided as an example of the determining unit that determines the contents of an answer of the interlocutor to a question of the user. However, only one of them may be provided. Further, when the information providing device 20 is a device having the single object of providing information, the object setting unit 21 may not be provided.

Figure 6:
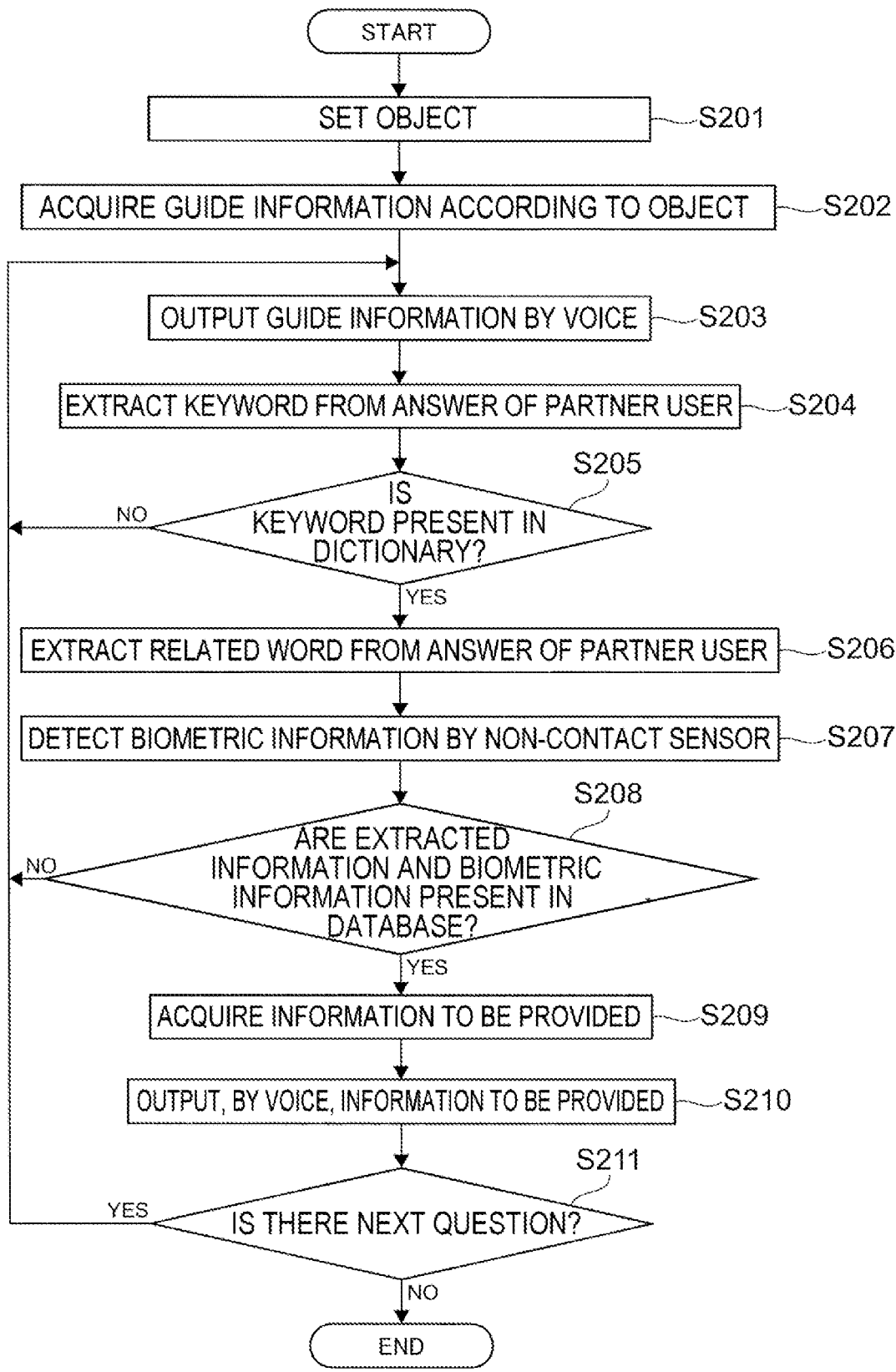
FIG. 6 is a flowchart illustrating an operation example of the information providing device according to the second exemplary embodiment of the invention in a first situation.

FIG. 6 is a flowchart illustrating an operation example of the information providing device 20 in the first situation according to the second exemplary embodiment.

As illustrated, in the information providing device 20, first, the object setting unit 21 sets the object of providing information (step 201).

Then, the guide information acquisition unit 22 acquires the guide information according to the object set by the object setting unit 21 (step 202).

Next, the information output unit 27 outputs the guide information acquired in step 202 to the operating user by voice (step 203).

When the operating user asks the partner user a question while listening to this guide information and the partner user answers the question, the interaction content analysis unit 25 extracts a keyword from the answer (step 204). Then, it is determined whether or not the extracted keyword is registered in the object-specific dictionary (step 205).

When it is determined that the keyword is registered in the object-specific dictionary, the interaction content analysis unit 25 extracts a related word from the answer (step 206). Specifically, a related item registered in the object-specific dictionary in association with the keyword is acquired and a related word indicating the specific contents of the related item is extracted from the answer.

Meanwhile, the non-contact detection unit 23 uses the non-contact sensor to detect the biometric information of the partner user (step 207).

Then, the information acquisition unit 26 determines whether or not the pair of the information extracted in steps 204 and 206 and the biometric information detected in step 207 is registered in the database (step 208).

When it is determined that the pair of the extracted information and the biometric information is registered in the database, the information acquisition unit 26 acquires the information to be provided, which is registered in the database in association with this pair (step 209).

Next, the information output unit 27 outputs, to the operating user by voice, the information to be provided (step 210), which is acquired in step 209.

Thereafter, the interaction content analysis unit 25 determines whether or not the next question is included in the guide information (step 211). In addition, even when it is determined in step 205 that the keyword is not registered in the object-specific dictionary or even when it is determined in step 208 that the pair of the extracted information and the biometric information is not registered in the database, the interaction content analysis unit 25 determines whether or not the next question is included in the guide information (step 211). When it is determined that the next question is included in the guide information, the information providing device 20 returns the process to step 203 to repeat the subsequent steps. On the other hand, when it is determined that the next question is not included in the guide information, the information providing device 20 ends the process.

Figure 7:
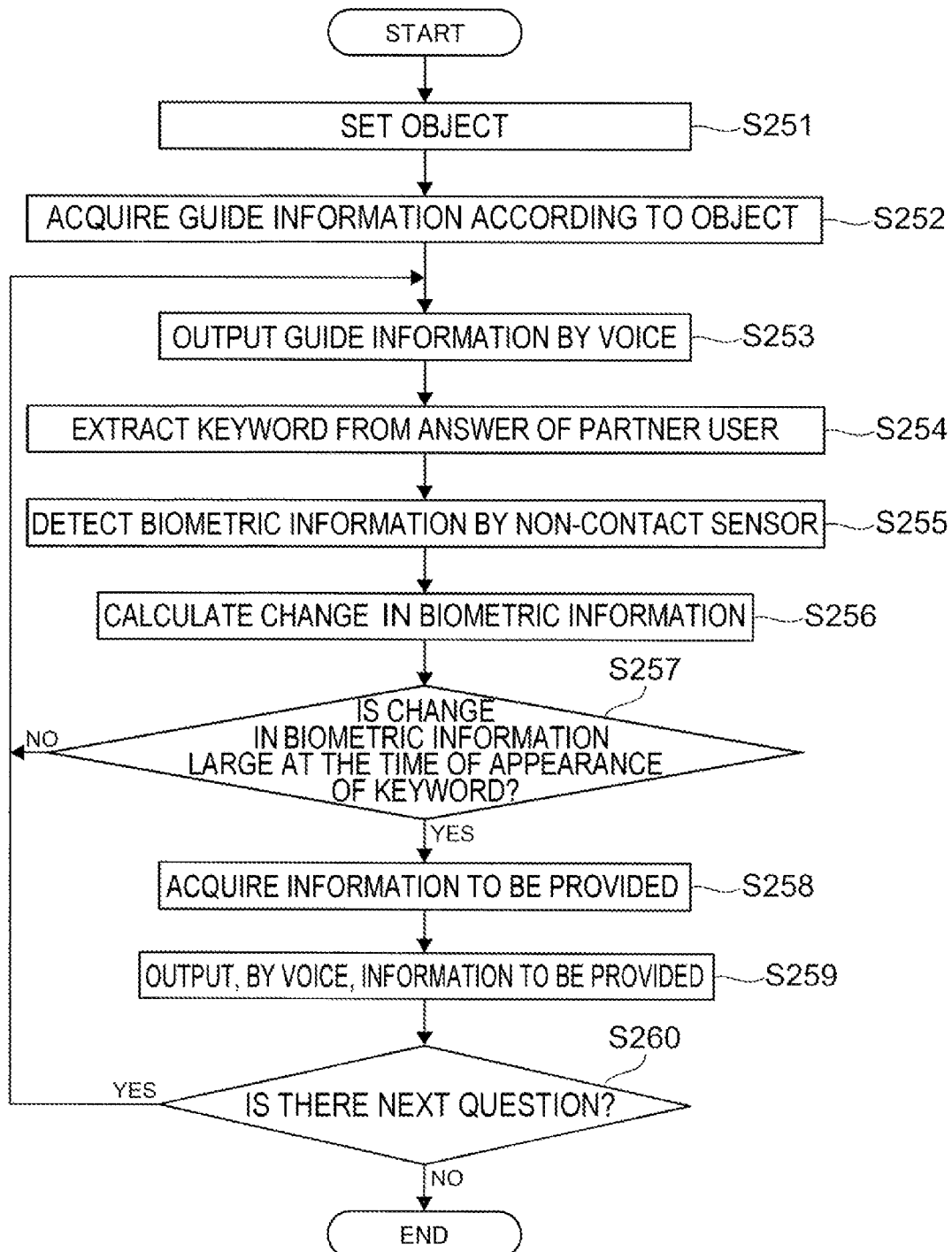
FIG. 7 is a flowchart illustrating an operation example of the information providing device according to the second exemplary embodiment of the invention in a second situation.

FIG. 7 is a flowchart illustrating an operation example of the information providing device 20 in the second situation in the second exemplary embodiment.

As illustrated, in the information providing device 20, first, the object setting unit 21 sets the object of providing information (step 251).

Then, the guide information acquisition unit 22 acquires the guide information according to the object set by the object setting unit 21 (step 252).

Next, the information output unit 27 outputs the guide information acquired in step 252 to the operating user by voice (step 253).

When the operating user asks the partner user a question while listening to this guide information and the partner user answers the question, the interaction content analysis unit 25 extracts a keyword from the answer (step 254).

Meanwhile, the non-contact detection unit 23 uses the non-contact sensor to detect the biometric information of the partner user (step 255). Then, the non-contact detection unit 23 calculates a change in the detected biometric information (step 256).

Then, the information acquisition unit 26 determines whether or not the change in the biometric information calculated in step 256 is large at the time of appearance of the keyword extracted in step 254 (step 257). Specifically, the information acquisition unit 26 determines whether or not the change in the biometric information calculated in step 256 is larger than a predetermined threshold value.

When it is determined that the change in the biometric information is large at the time of appearance of the keyword, the information acquisition unit 26 acquires information to be provided according to this keyword (step 258).

Next, the information output unit 27 outputs, to the operating user by voice, the information to be provided (step 259), which is acquired in step 258.

Thereafter, the interaction content analysis unit 25 determines whether or not the next question is included in the guide information (step 260). Even when it is determined in step 257 that the change in the biometric information is not large at the time of appearance of the keyword, the interaction content analysis unit 25 determines whether or not the next question is included in the guide information (step 260). When it is determined that the next question is included in the guide information, the information providing device 20 returns the process to step 253 to repeat the subsequent steps. On the other hand, when it is determined that the next question is not included in the guide information, the information providing device 20 ends the process.

In the case described above, after outputting, by voice, a portion of the guide information that guides a specific question, the information output unit 27 outputs, by voice, information to be provided according to an answer of the partner user to the question asked by the operating user who is listening to that portion of the guide information, and then outputs, by voice, a portion of the guide information that guides the next question, although the invention is not limited in this respect. Alternatively, after outputting, by voice, a portion of the guide information that guides a specific question, the information output unit 27 may output a portion of the guide information that guides the next question before outputting, by voice, information to be provided according to an answer of the partner user to the question asked by the operating user who is listening to that portion of the guide information.

However, in this case, there is a possibility that a situation may occur in which the guide information output by voice by the information output unit 27 does not match the information to be provided. For this situation, it is conceivable to perform the following three controls.

The first control is that, after starting output of a portion of the guide information that guides the next question, the information output unit 27 does not output, to the operating user by voice, the information to be provided according to the answer of the partner user to the question asked by the operating user who is listening to the portion of the guide information, which guides a certain question. This is a control that does not allow the situation where the guide information does not match the information to be provided, and is based on the idea that the information to be provided about the already finished question should be discarded.

The second control is that, during a period from the start of outputting by voice a portion of the guide information that guides the next question to the end of outputting the whole of the portion of the guide information, the information output unit 27 outputs, to the operating user by voice, the information to be provided according to the answer of the partner user to the question asked by the operating user who is listening to the portion of the guide information, which guides a certain question. This is a control that allows the situation where the guide information does not match the information to be provided.

The third control is that, after ending output of the whole of the portion of the guide information, the information output unit 27 outputs, to the operating user by voice, the information to be provided according to the answer of the partner user to the question asked by the operating user who is listening to the portion of the guide information, which guides a certain question. This is a control that does not allow the situation where the guide information does not match the information to be provided, and is based on the idea that the information to be provided about the already finished question should be collectively transmitted at the end.

In the above description concerning the controls, the "next question" is an example of a "specific question", and a "certain question" is an example of a "question before the specific question".

Third Exemplary Embodiment

Figure 8:
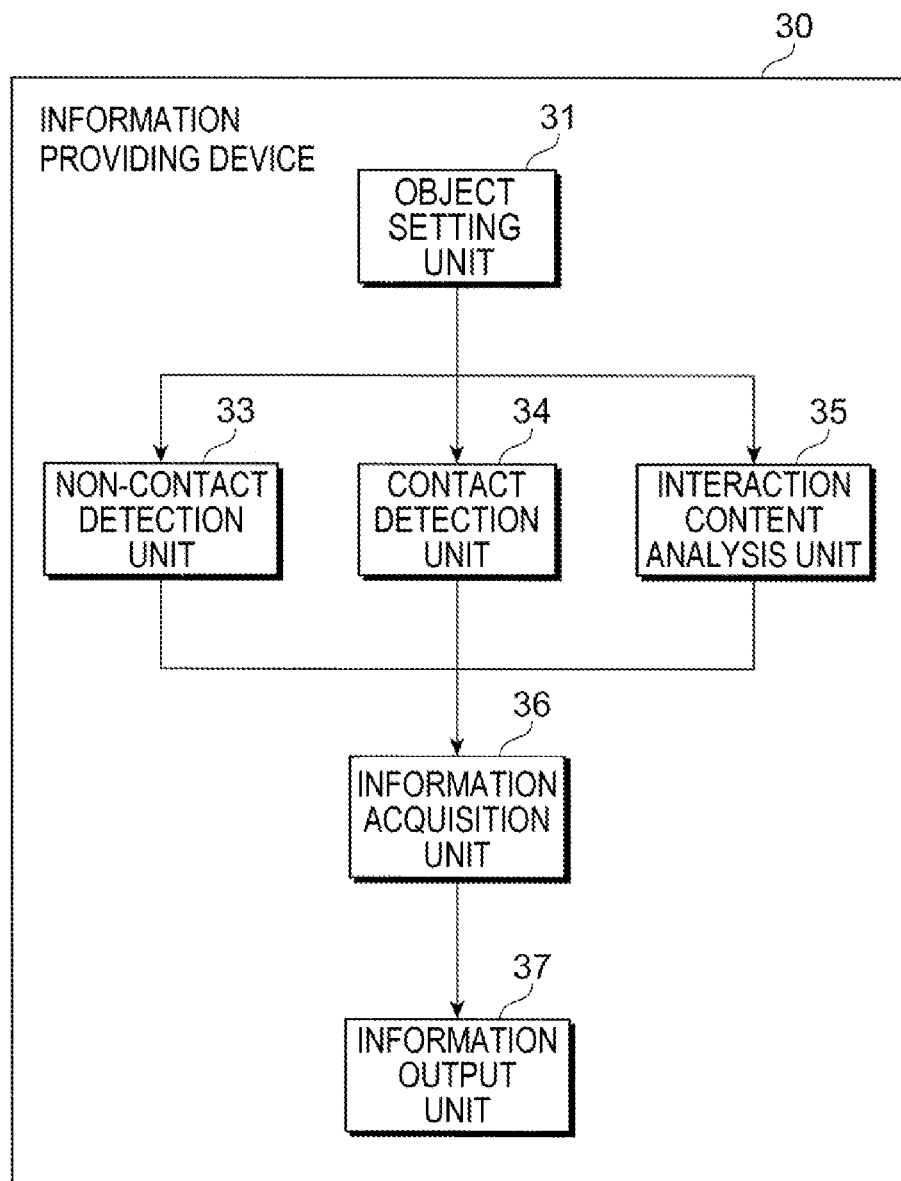
FIG. 8 is a block diagram illustrating a functional configuration example of an information providing device according to a third exemplary embodiment of the invention.

FIG. 8 is a block diagram illustrating a functional configuration example of an information providing device 30 according to a third exemplary embodiment. As illustrated, the information providing device 30 according to the third exemplary embodiment includes an object setting unit 31, a non-contact detection unit 33, a contact detection unit 34, an interaction content analysis unit 35, an information acquisition unit 36 and an information output unit 37.

The object setting unit 31, the non-contact detection unit 33, the interaction content analysis unit 35 and the information output unit 37 correspond respectively to the object setting unit 11, the non-contact detection unit 13, the interaction content analysis unit 15 and the information output unit 17 in the first exemplary embodiment, and therefore, explanation thereof will not be repeated.

The contact detection unit 34, which is connected to a contact sensor (not illustrated) capable of measuring biometric information in such a manner as to directly contact with the body of the partner user, acquires the biometric information detected by the contact sensor, and provides, as detected information, the biometric information or a calculated temporal change in the biometric information. Here, the contact sensor used may be one capable of measuring, for example, body temperature, pulsation, or the like. For consultation, the contact detection unit 34 determines the body temperature, pulsation or the like of the partner user as detected information. For sales or maintenance, the contact detection unit 34 determines a calculated temporal change in the body temperature, pulsation or the like of the partner user as detected information. In the exemplary embodiment, the contact sensor is used as an example of a contact detector that detects the physical condition of the interlocutor while contacting with the body of the interlocutor, and the contact detection unit 34 is provided as an example of a determining unit that determines the physical condition of the interlocutor or a change in the condition using the contact detector.

The information acquisition unit 36 collates the biometric information or a change in the biometric information, which is information detected by the non-contact detection unit 33 and the contact detection unit 34, with the extracted information or the keyword, which is extracted by the interaction content analysis unit 35, to acquire the information to be provided. Here, the "biometric information set as the detection information detected by the non-contact detection unit 33 and the contact detection unit 34" may be a simple combination of the biometric information set as the detection information detected by the non-contact detection unit 33 and the biometric information set as the detection information detected by the contact detection unit 34 or may be biometric information newly obtained from the biometric information set as the detection information detected by the non-contact detection unit 33 and the biometric information set as the detection information detected by the contact detection unit 34.

In the first situation, the information acquisition unit 36 determines whether or not the information to be provided is registered in association with the extracted information and the biometric information in an object-specific database. When it is determined that the information to be provided is registered, the information acquisition unit 36 acquires the information to be provided. For consultation, for example, when the information to be provided, such as a lifestyle habit having adverse effect on a symptom or a medicine that will be prescribed for the symptom, is registered in association with the extracted information and the biometric information in a database for each symptom, the information acquisition unit 36 acquires the information to be provided.

In the second situation, when a change in the biometric information is large at the time of appearance of a keyword in the contents of an answer, the information acquisition unit 36 acquires the information to be provided according to the keyword. For sales and maintenance, for example, the information acquisition unit 36 may acquire, as the information to be provided, a keyword appearing when the change in the biometric information is significant.

In the third exemplary embodiment, the non-contact detection unit 33, the contact detection unit 34 and the interaction content analysis unit 35 are provided as an example of the determining unit that determines the contents of an answer of the interlocutor to a question of the user. However, only one or two of them may be provided. Further, when the information providing device 30 is a device having the single object of providing information, the object setting unit 31 may not be provided.

Figure 9:
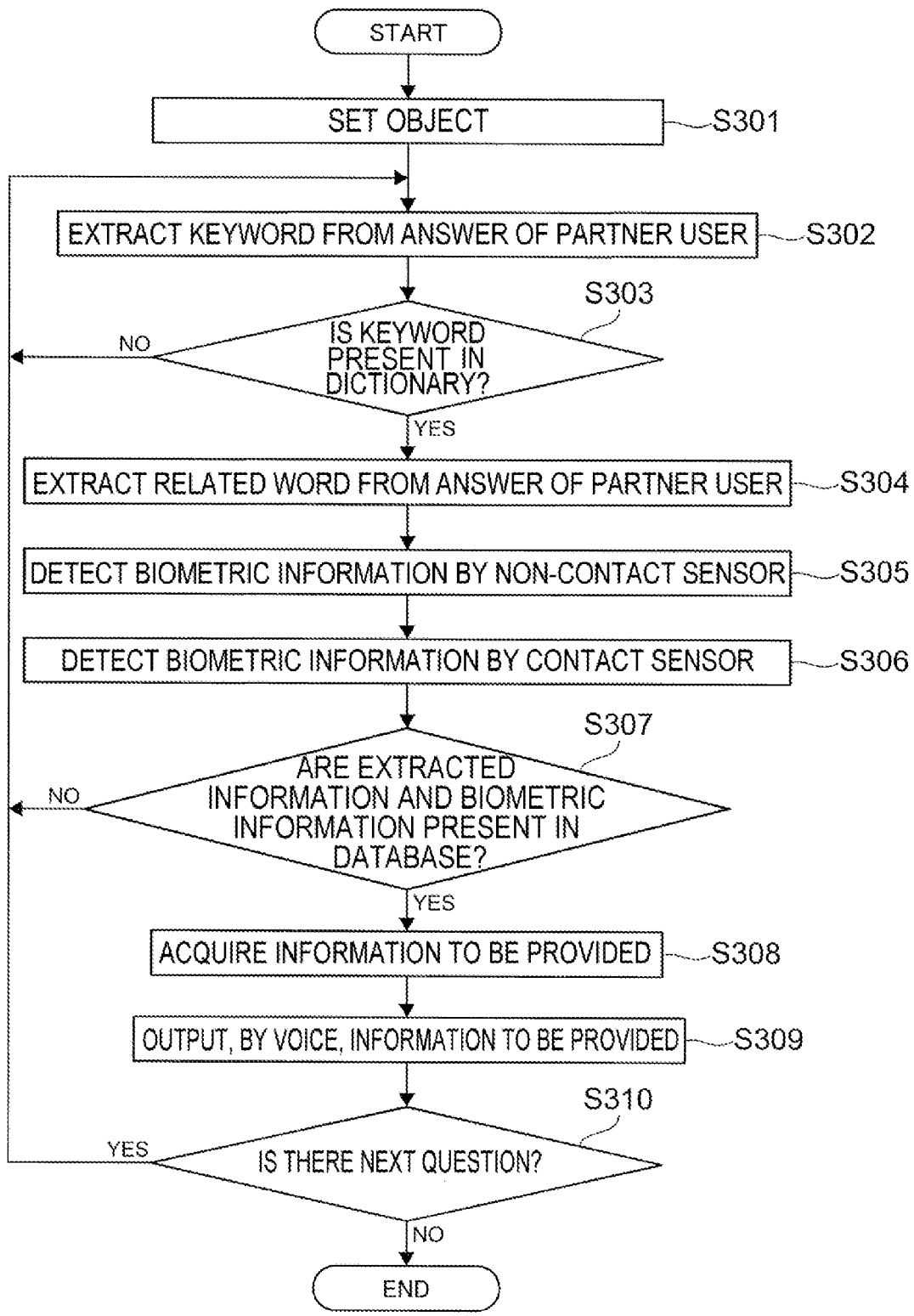
FIG. 9 is a flowchart illustrating an operation example of the information providing device according to the third exemplary embodiment of the invention in a first situation.

FIG. 9 is a flowchart illustrating an operation example of an information providing device 30 in the first situation in the third exemplary embodiment.

As illustrated, in the information providing device 30, first, the object setting unit 31 sets the object of providing information (step 301).

In this state, when the operating user asks the partner user a question and the partner user answers the question, the interaction content analysis unit 35 extracts a keyword from the answer (step 302). Then, it is determined whether or not the extracted keyword is registered in the object-specific dictionary (step 303).

When it is determined that the keyword is registered in the object-specific dictionary, the interaction content analysis unit 35 extracts a related word from the answer (step 304). Specifically, a related item registered in the object-specific dictionary in association with the keyword is acquired and a related word indicating the specific contents of the related item is extracted from the answer.

Meanwhile, the non-contact detection unit 33 uses the non-contact sensor to detect the biometric information of the partner user (step 305).

In addition, the contact detection unit 34 uses the contact sensor to detect the biometric information of the partner user (step 306).

Then, the information acquisition unit 36 determines whether or not the pair of the information extracted in steps 302 and 304 and the biometric information detected in steps 305 and 306 is registered in the database (step 307).

When it is determined that the pair of the extracted information and the biometric information is registered in the database, the information acquisition unit 36 acquires the information to be provided, which is registered in the database in association with the pair (step 308).

Next, the information output unit 37 outputs, to the operating user by voice, the information to be provided (step 309), which is acquired in step 308.

Thereafter, the interaction content analysis unit 35 determines whether or not the operating user is asking the partner user the next question (step 310). In addition, even when it is determined in step 303 that the keyword is not registered in the object-specific dictionary or even when it is determined in step 307 that the pair of the extracted information and the biometric information is not registered in the database, the interaction content analysis unit 35 determines whether or not the operating user is asking the partner user the next question (step 310). When it is determined that the operating user is asking the partner user the next question, the information providing device 30 returns the process to step 302 to repeat the subsequent steps. On the other hand, when it is determined that the operating user is not asking the partner user the next question, the information providing device 30 ends the process.

Figure 10:
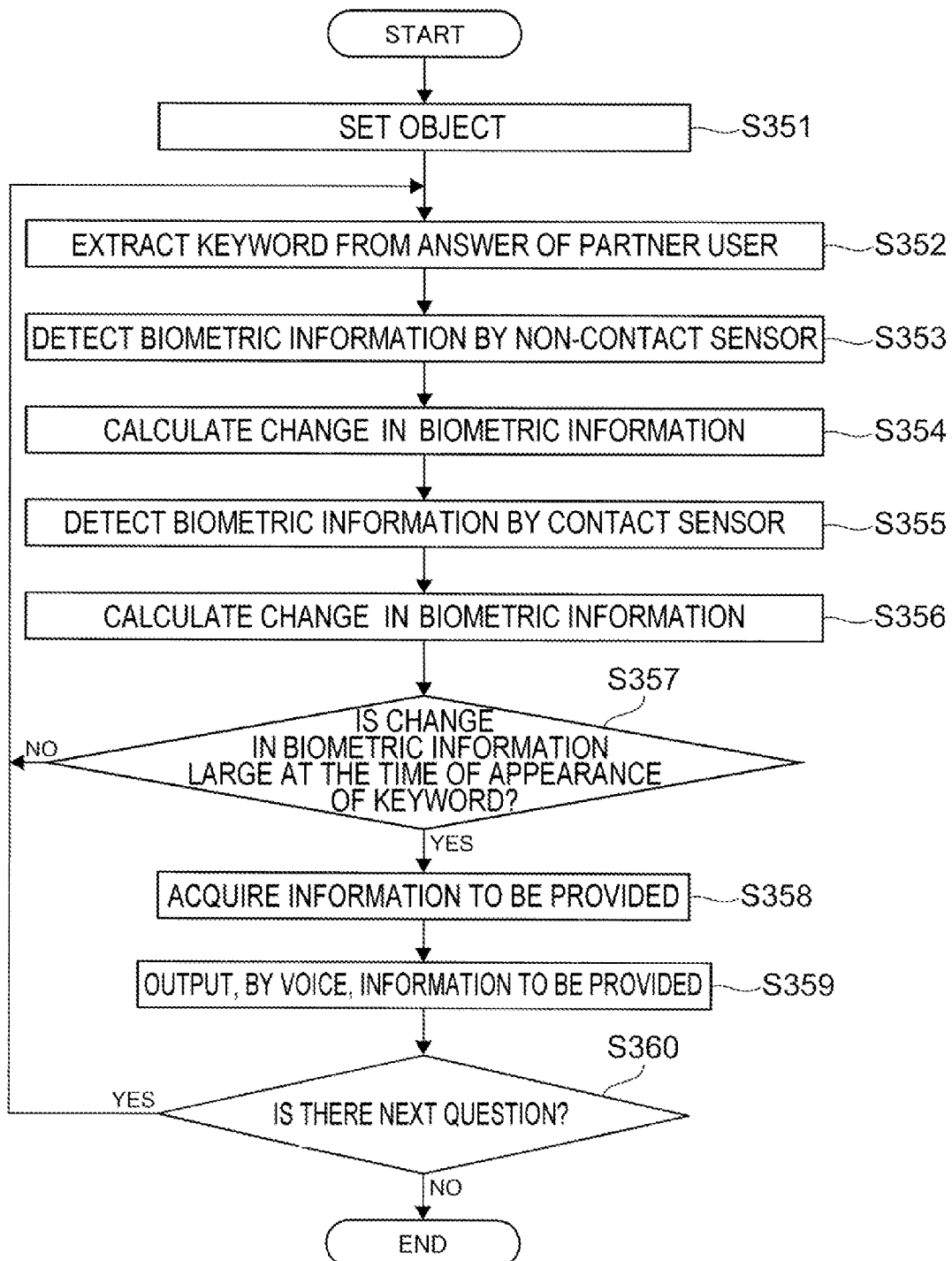
FIG. 10 is a flowchart illustrating an operation example of the information providing device according to the third exemplary embodiment of the invention in a second situation.

FIG. 10 is a flowchart illustrating an operation example of the information providing device 30 in the second situation in the third exemplary embodiment.

As illustrated, in the information providing device 30, first, the object setting unit 31 sets the object of providing information (step 351).

In this state, when the operating user asks the partner user a question and the partner user answers the question, the interaction content analysis unit 35 extracts a keyword from the answer (step 352).

Meanwhile, the non-contact detection unit 33 uses the non-contact sensor to detect the biometric information of the partner user (step 353). Then, the non-contact detection unit 33 calculates a change in the detected biometric information (step 354).

In addition, the contact detection unit 34 uses the contact sensor to detect the biometric information of the partner user (step 355). Then, the contact detection unit 34 calculates a change in the detected biometric information (step 356).

Then, the information acquisition unit 36 determines whether or not the change in the biometric information calculated in step 354 and step 356 is large at the time of appearance of the keyword extracted in step 352 (step 357). Specifically, the information acquisition unit 36 determines whether or not the change in the biometric information calculated in step 354 and step 356 is larger than a predetermined threshold value.

When it is determined that the change in the biometric information is large at the time of appearance of the keyword, the information acquisition unit 36 acquires information to be provided according to the keyword (step 358).

Next, the information output unit 37 outputs, to the operating user by voice, the information to be provided (step 359), which is acquired in step 358.

Thereafter, the interaction content analysis unit 35 determines whether or not the operating user is asking the partner user the next question (step 360). Even when it is determined in step 357 that the change in the biometric information is not large at the time of appearance of the keyword, the interaction content analysis unit 35 determines whether or not the operating user is asking the partner user the next question (step 360). When it is determined that the operating user is asking the partner user the next question, the information providing device 30 returns the process to step 352 to repeat the subsequent steps. On the other hand, when it is determined that the operating user is not asking the partner user the next question, the information providing device 30 ends the process.

Fourth Exemplary Embodiment

Figure 11:
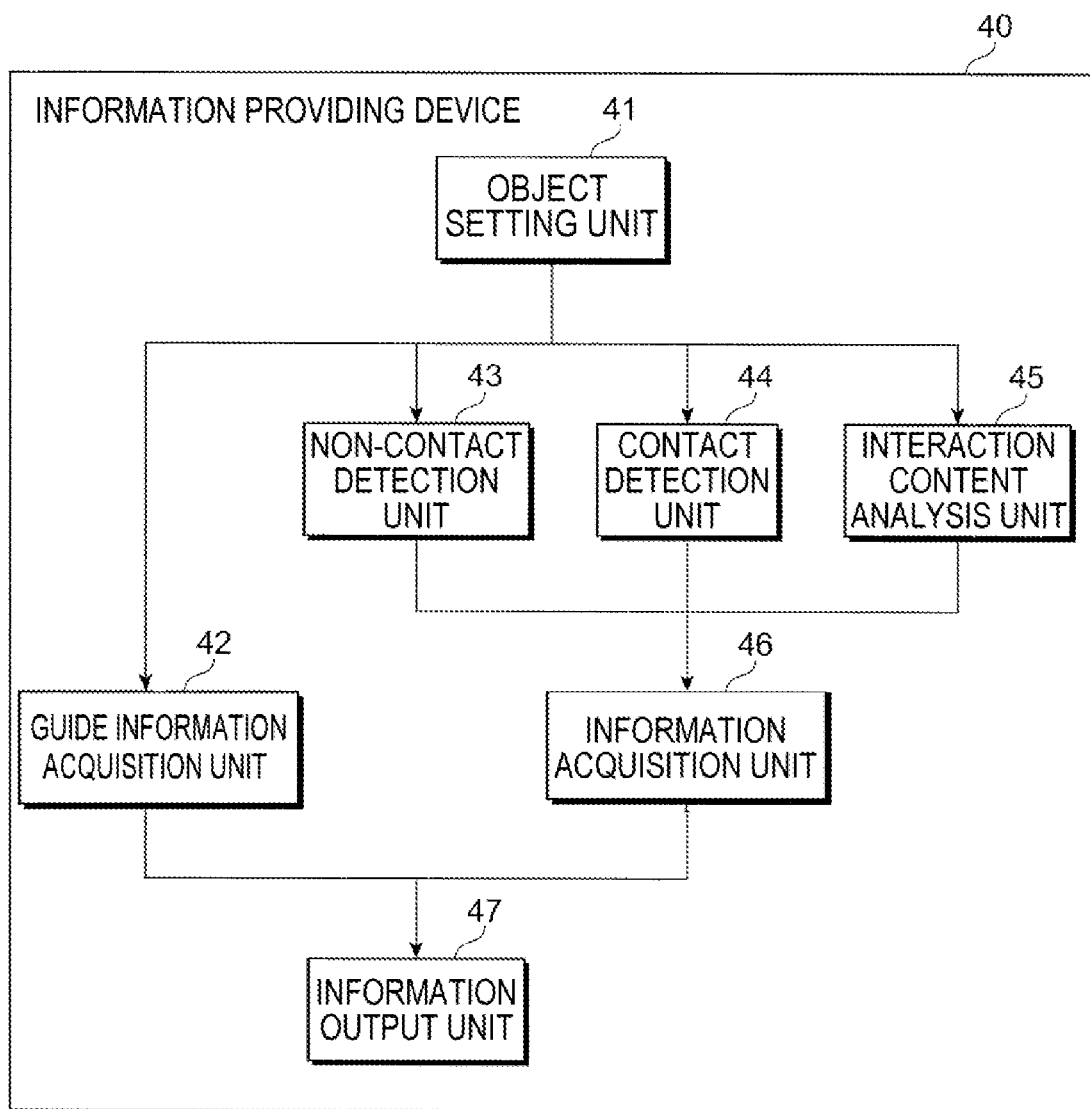
FIG. 11 is a block diagram illustrating a functional configuration example of an information providing device according to a fourth exemplary embodiment of the invention.

FIG. 11 is a block diagram illustrating a functional configuration example of an information providing device 40 according to a fourth exemplary embodiment. As illustrated, the information providing device 40 according to the fourth exemplary embodiment includes an object setting unit 41, a guide information acquisition unit 42, a non-contact detection unit 43, a contact detection unit 44, an interaction content analysis unit 45, an information acquisition unit 46 and an information output unit 47.

The object setting unit 41, the non-contact detection unit 43 and the interaction content analysis unit 45 correspond respectively to the object setting unit 11, the non-contact detection unit 13 and the interaction content analysis unit 15 in the first exemplary embodiment and therefore, explanation will not be repeated. The guide information acquisition unit 42 and the information output unit 47 correspond respectively to the guide information acquisition unit 22 and the information output unit 27 in the second exemplary embodiment and therefore, explanation will not be repeated. The contact detection unit 44 and the information acquisition unit 46 correspond respectively to the contact detection unit 34 and the information acquisition unit 36 in the third exemplary embodiment and therefore, explanation will not be repeated.

In the fourth exemplary embodiment, the non-contact detection unit 43, the contact detection unit 44 and the interaction content analysis unit 45 are provided as an example of the determining unit that determines the contents of an answer of the interlocutor to a question of the user. However, only one or two of them may be provided. Further, when the information providing device 40 is a device having a single object to provide information, the object setting unit 41 may not be provided.

Figure 12:
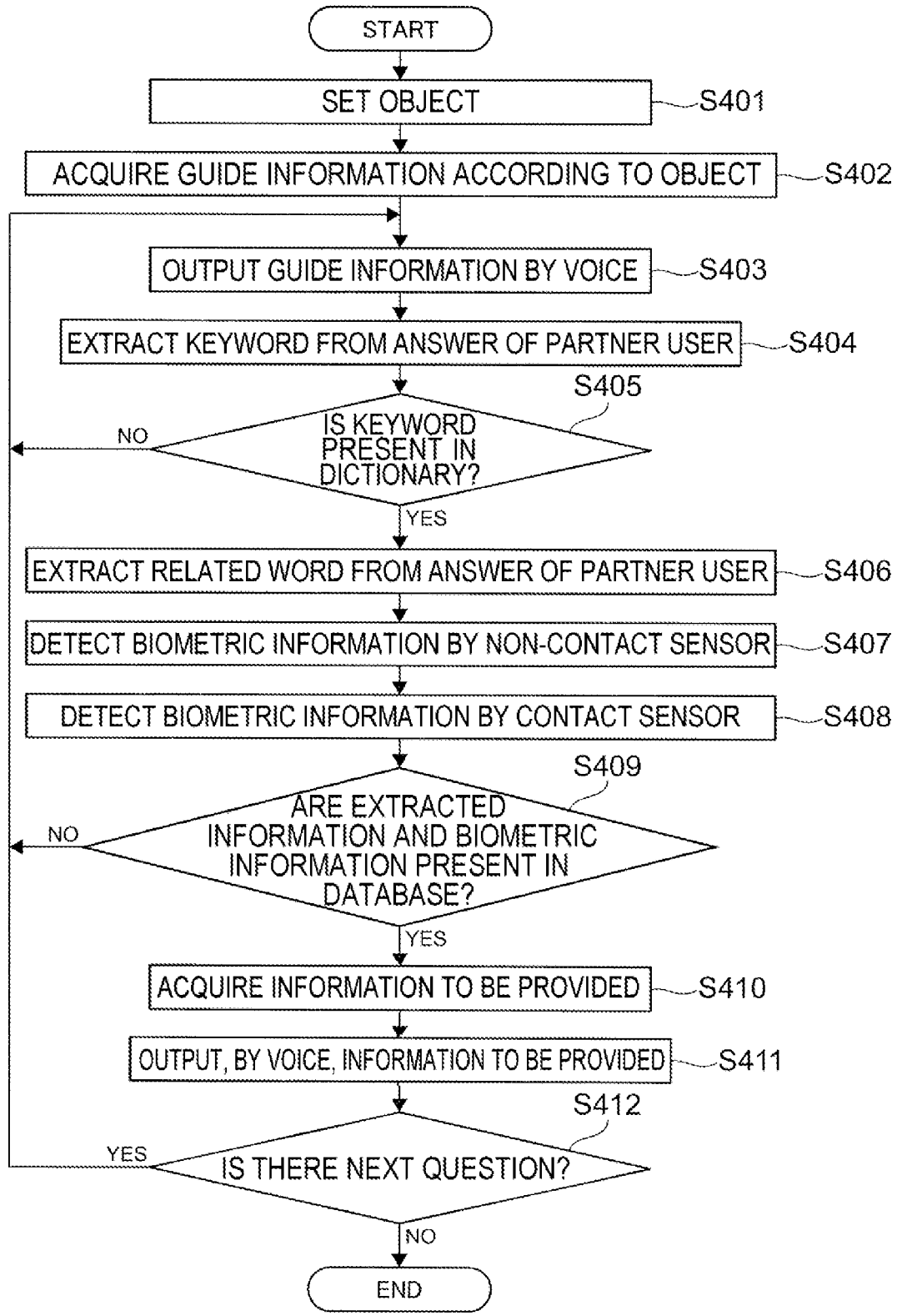
FIG. 12 is a flowchart illustrating an operation example of the information providing device according to the fourth exemplary embodiment of the invention in a first situation.

FIG. 12 is a flowchart illustrating an operation example of the information providing device 40 in the first situation according to the fourth exemplary embodiment.

As illustrated, in the information providing device 40, first, the object setting unit 41 sets the object of providing information (step 401).

Then, the guide information acquisition unit 42 acquires the guide information according to the object set by the object setting unit 41 (step 402).

Next, the information output unit 47 outputs the guide information acquired in step 402 to the operating user by voice (step 403).

While listening to this guide information, when the operating user asks the partner user a question and the partner user answers the question, the interaction content analysis unit 45 extracts a keyword from the answer (step 404). Then, it is determined whether or not the extracted keyword is registered in the object-specific dictionary (step 405).

When it is determined that the keyword is registered in the object-specific dictionary, the interaction content analysis unit 45 extracts a related word from the answer (step 406). Specifically, a related item registered in the object-specific dictionary in association with the keyword is acquired and a related word indicating the specific contents of the related item is extracted from the answer.

Meanwhile, the non-contact detection unit 43 uses the non-contact sensor to detect the biometric information of the partner user (step 407).

In addition, the contact detection unit 44 uses the contact sensor to detect the biometric information of the partner user (step 408).

Then, the information acquisition unit 46 determines whether or not the pair of the information extracted in steps 404 and 406 and the biometric information detected in steps 407 and 408 is registered in the database (step 409).

When it is determined that the pair of the extracted information and the biometric information is registered in the database, the information acquisition unit 46 acquires the information to be provided, which is registered in the database in association with this pair (step 410).

Next, the information output unit 47 outputs, to the operating user by voice, the information to be provided (step 411), which is acquired in step 410.

Thereafter, the interaction content analysis unit 45 determines whether or not the next question is included in the guide information (step 412). In addition, even when it is determined in step 405 that the keyword is not registered in the object-specific dictionary or even when it is determined in step 409 that the pair of the extracted information and the biometric information is not registered in the database, the interaction content analysis unit 45 determines whether or not the next question is included in the guide information (step 412). When it is determined that the next question is included in the guide information, the information providing device 40 returns the process to step 403 to repeat the subsequent steps. On the other hand, when it is determined that the next question is not included in the guide information, the information providing device 40 ends the process.

Figure 13:
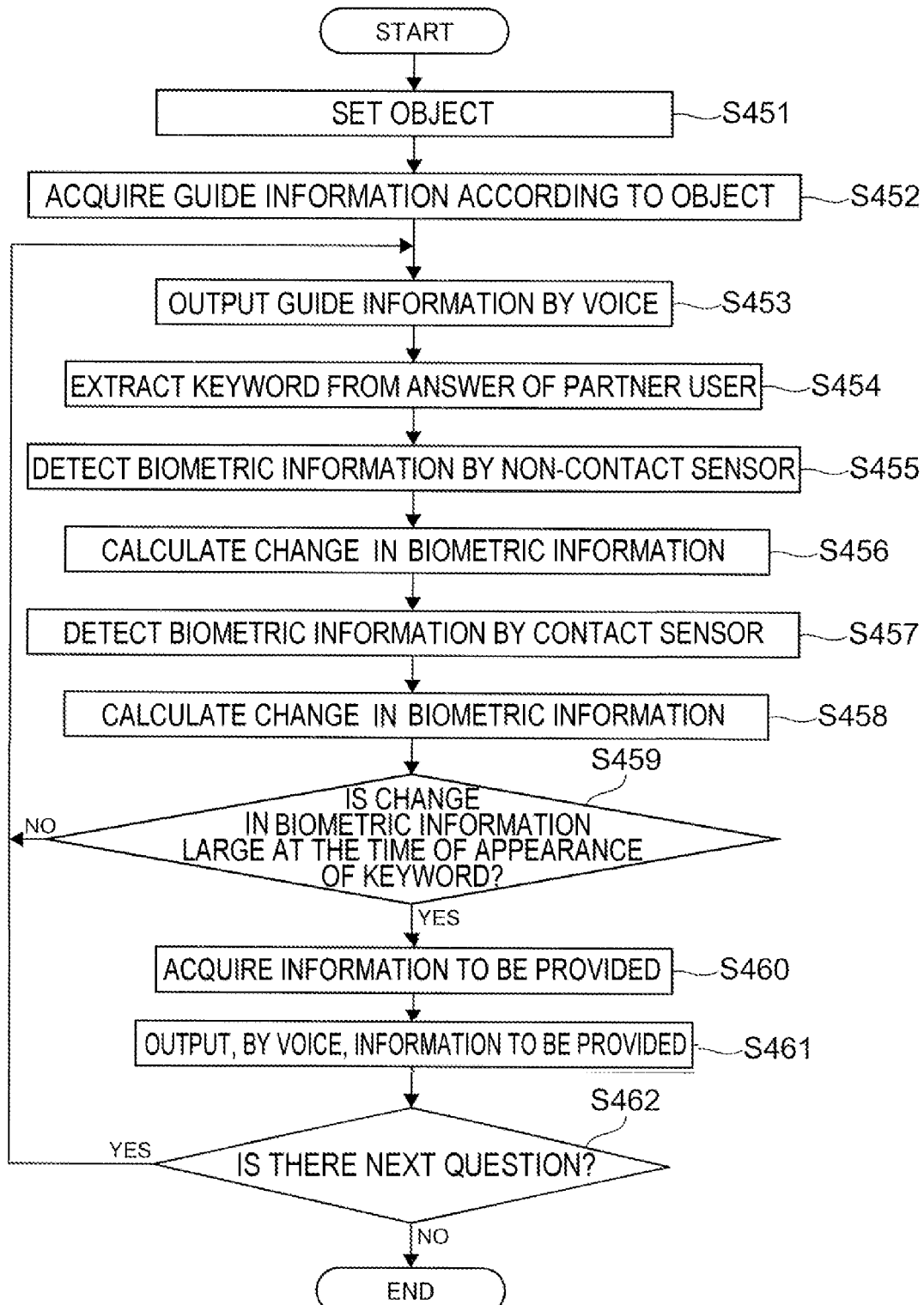
FIG. 13 is a flowchart illustrating an operation example of the information providing device according to the fourth exemplary embodiment of the invention in a second situation.

FIG. 13 is a flowchart illustrating an operation example of the information providing device 40 in the second situation in the fourth exemplary embodiment.

As illustrated, in the information providing device 40, first, the object setting unit 41 sets the object of providing information (step 451).

Then, the guide information acquisition unit 42 acquires the guide information according to the object set by the object setting unit 41 (step 452).

Next, the information output unit 47 outputs the guide information acquired in step 452 to the operating user by voice (step 453).

While listening to this guide information, when the operating user asks the partner user a question and the partner user answers the question, the interaction content analysis unit 45 extracts a keyword from the answer (step 454).

Meanwhile, the non-contact detection unit 43 uses the non-contact sensor to detect the biometric information of the partner user (step 455). Then, the non-contact detection unit 43 calculates a change in the detected biometric information (step 456).

Meanwhile, the contact detection unit 44 uses the contact sensor to detect the biometric information of the partner user (step 457). Then, the contact detection unit 44 calculates a change in the detected biometric information (step 458).

Then, the information acquisition unit 46 determines whether or not the change in the biometric information calculated in steps 456 and 458 is large at the time of appearance of the keyword extracted in step 454 (step 459). Specifically, the information acquisition unit 46 determines whether or not the change in the biometric information calculated in steps 456 and 458 is larger than a predetermined threshold value.

When it is determined that the change in the biometric information is large at the time of appearance of the keyword, the information acquisition unit 46 acquires information to be provided according to the keyword (step 460).

Next, the information output unit 47 outputs, to the operating user by voice, the information to be provided (step 461), which is acquired in step 460.

Thereafter, the interaction content analysis unit 45 determines whether or not the next question is included in the guide information (step 462). Even when it is determined in step 459 that the change in the biometric information is not large at the time of appearance of the keyword, the interaction content analysis unit 45 determines whether or not the next question is included in the guide information (step 462). When it is determined that the next question is included in the guide information, the information providing device 40 returns the process to step 453 to repeat the subsequent steps. On the other hand, when it is determined that the next question is not included in the guide information, the information providing device 40 ends the process.

Fifth Exemplary Embodiment

Figure 14:
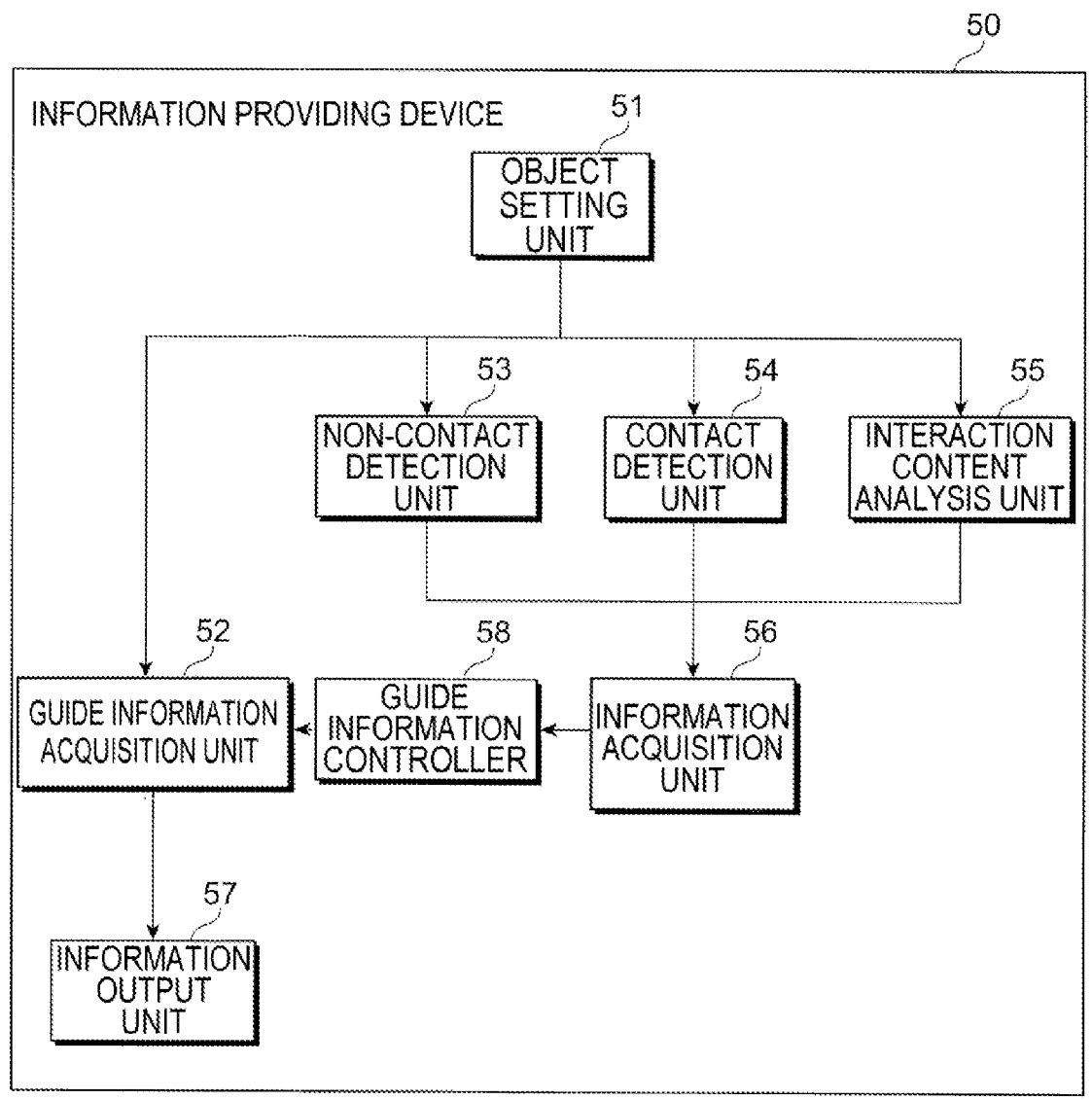
FIG. 14 is a block diagram illustrating a functional configuration example of an information providing device according to a fifth exemplary embodiment of the invention.

FIG. 14 is a block diagram illustrating a functional configuration example of an information providing device 50 according to a fifth exemplary embodiment. As illustrated, the information providing device 50 according to the fifth exemplary embodiment includes an object setting unit 51, a guide information acquisition unit 52, a non-contact detection unit 53, a contact detection unit 54, an interaction content analysis unit 55, an information acquisition unit 56, an information output unit 57 and a guide information controller 58.

The object setting unit 51, the non-contact detection unit 53 and the interaction content analysis unit 55 correspond respectively to the object setting unit 11, the non-contact detection unit 13 and the interaction content analysis unit 15 in the first exemplary embodiment and therefore, explanation will not be repeated. The guide information acquisition unit 52 corresponds to the guide information acquisition unit 22 in the second exemplary embodiment and therefore, explanation will not be repeated. The contact detection unit 54 and the information acquisition unit 56 correspond respectively to the contact detection unit 34 and the information acquisition unit 36 in the third exemplary embodiment and therefore, explanation will not be repeated.

The guide information controller 58 uses the information to be provided, which is acquired by the information acquisition unit 56, to change the guide information acquired by the guide information acquisition unit 52. A method of changing the guide information will be described by taking the contents of the conversation illustrated in FIGS. 1A to 1C as an example.

For consultation, for example, the conversation of FIG. 1A is made. In addition, at the point of time when the patient answers "Yes" to the question "Do you drink alcohol?" asked by the doctor, the guide information scheduled to be output by the information output unit 57 is, for example, guide information to advance dialogue toward refraining from drinking alcohol. However, after that, in response to the question "How often and how much?" asked by the doctor, the patient answers "About 0.4 pints of Sake every night". In this case, when the physical condition of the patient is such that the blood pressure and the pulse rate are high, the guide information controller 58 changes the guide information to be output by the information output unit 57 to guide information to advance dialogue toward, for example, refraining from drinking and receiving detailed examination.

For sales, for example, the conversation of FIG. 1B is made. In addition, at the point of time when the customer answers "Unmarried" to the question "Married or unmarried?" asked by the salesman, the guide information scheduled to be output by the information output unit 57 is, for example, guide information to ask a performance-oriented question. However, after that, in response to the question "How much space do you currently have for installing a refrigerator?" asked by the salesman, the customer answers "About XX?". Then, in response to the question "How much is your budget?" asked by the salesman, the customer answers "About YY Yen". At the time of these answers, for example, there is a large change in the customer's physical condition. Regarding the installation space, there is a possibility that the change in the physical condition is large because of the ambiguous answer of "About XX?", and thus, it is unclear whether the answer is in line with the actual intention of the customer. However, regarding the budget, since the change in the customer's physical condition is large despite the clear answer "About YY Yen", there is a possibility that the answer presents a high budget against the actual intention. Thus, the salesman should advance dialogue toward keeping the budget low. Therefore, the guide information controller 58 changes the guide information to be output by the information output unit 57 to, for example, guide information to ask a budget-oriented question.

For maintenance, for example, the conversation of FIG. 1C is made. In addition, the guide information initially scheduled to be output by the information output unit 57 is guide information to ask a question such as "The sheet is a continuous sheet or a cut sheet?". However, in this case, the customer answers "Yes" to the question "Have sheets been fed from those set in the cassette?" asked by the maintenance man. At the time of this answer, if there is a large change in the customer's physical condition, the answer may contradict the facts. Thus, the maintenance man should check whether or not the sheets have been manually fed, whether or not the sheets have absorbed moisture, or the like. Therefore, the guide information controller 58 changes the guide information to be output by the information output unit 57 to guide information to check the surrounding humidity conditions, such as "Has an air conditioner been turned on?".

The information output unit 57 outputs the guide information acquired by the guide information acquisition unit 52 and changed by the guide information controller 58 to the operating user. In the case described below, the guide information is output by voice through a sound output unit 97 (see FIG. 17), although the invention is not limited in this respect. In the exemplary embodiment, the information output unit 57 is provided as an example of a transmission unit that transmits, to the user, instruction information changed based on the information to be provided.

Figure 15:
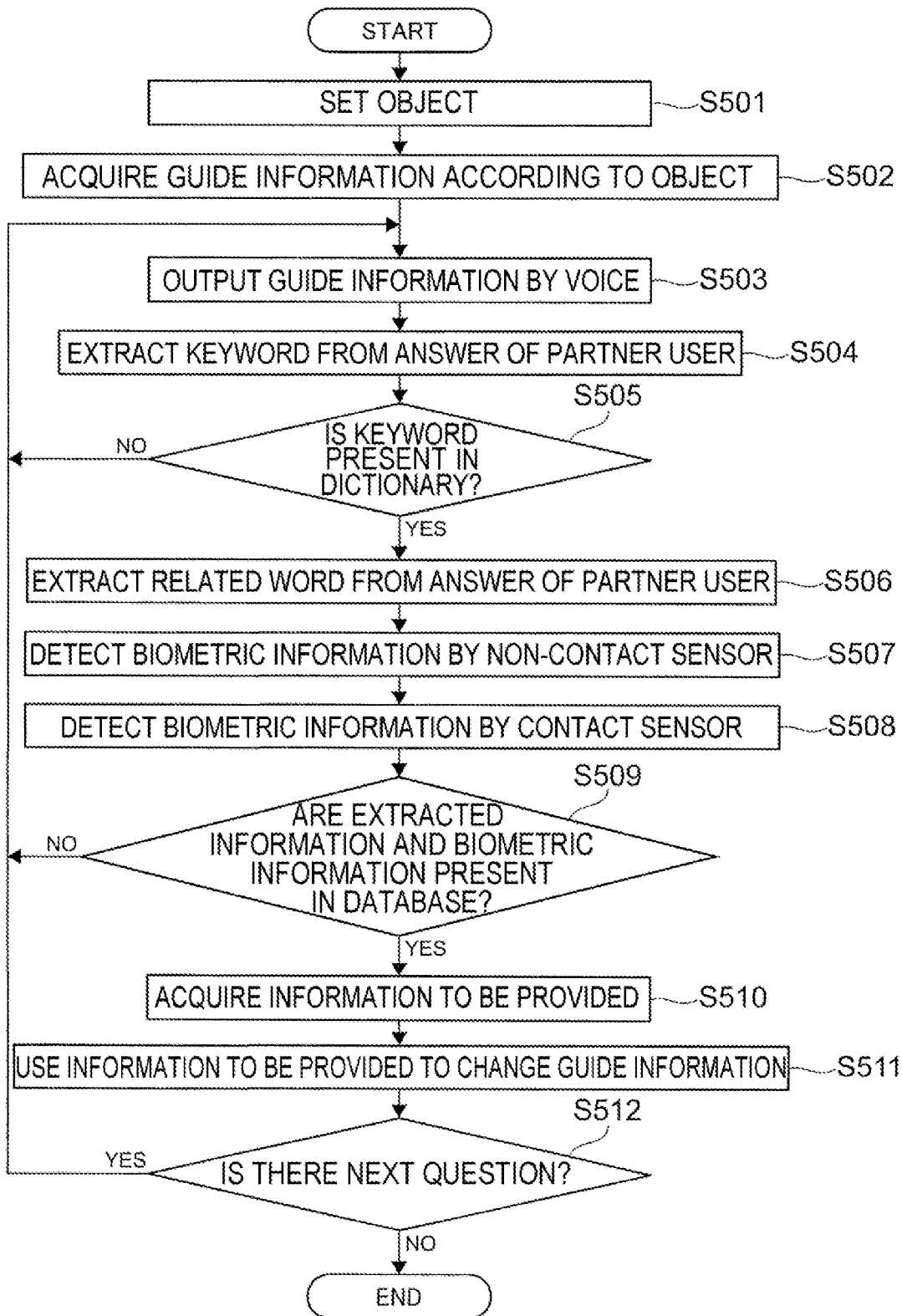
FIG. 15 is a flowchart illustrating an operation example of the information providing device according to the fifth exemplary embodiment of the invention in a first situation.

FIG. 15 is a flowchart illustrating an operation example of the information providing device 50 in the first situation according to the fifth exemplary embodiment.

As illustrated, in the information providing device 50, first, the object setting unit 51 sets the object of providing information (step 501).

Then, the guide information acquisition unit 52 acquires the guide information according to the object set by the object setting unit 51 (step 502).

Next, the information output unit 57 outputs the guide information acquired in step 502 to the operating user by voice (step 503).

While listening to this guide information, when the operating user asks the partner user a question and the partner user answers the question, the interaction content analysis unit 55 extracts a keyword from the answer (step 504). Then, it is determined whether or not the extracted keyword is registered in the object-specific dictionary (step 505).

When it is determined that the keyword is registered in the object-specific dictionary, the interaction content analysis unit 55 extracts a related word from the answer (step 506). Specifically, a related item registered in the object-specific dictionary in association with the keyword is acquired and a related word indicating the specific contents of the related item is extracted from the answer.

Meanwhile, the non-contact detection unit 53 uses the non-contact sensor to detect the biometric information of the partner user (step 507).

In addition, the contact detection unit 54 uses the contact sensor to detect the biometric information of the partner user (step 508).

Then, the information acquisition unit 56 determines whether or not the pair of the information extracted in steps 504 and 506 and the biometric information detected in steps 507 and 508 is registered in the database (step 509).

When it is determined that the pair of the extracted information and the biometric information is registered in the database, the information acquisition unit 56 acquires the information to be provided, which is registered in the database in association with this pair (step 510).

Next, the guide information controller 58 uses the information to be provided, which is acquired in step 510, to change the guide information acquired in step 502 (step 511).

Thereafter, the interaction content analysis unit 55 determines whether or not the next question is included in the guide information (step 512). In addition, even when it is determined in step 505 that the keyword is not registered in the object-specific dictionary or even when it is determined in step 509 that the pair of the extracted information and the biometric information is not registered in the database, the interaction content analysis unit 55 determines whether or not the next question is included in the guide information (step 512). When it is determined that the next question is included in the guide information, the information providing device 50 returns the process to step 503 to repeat the subsequent steps. On the other hand, when it is determined that the next question is not included in the guide information, the information providing device 50 ends the process.

Figure 16:
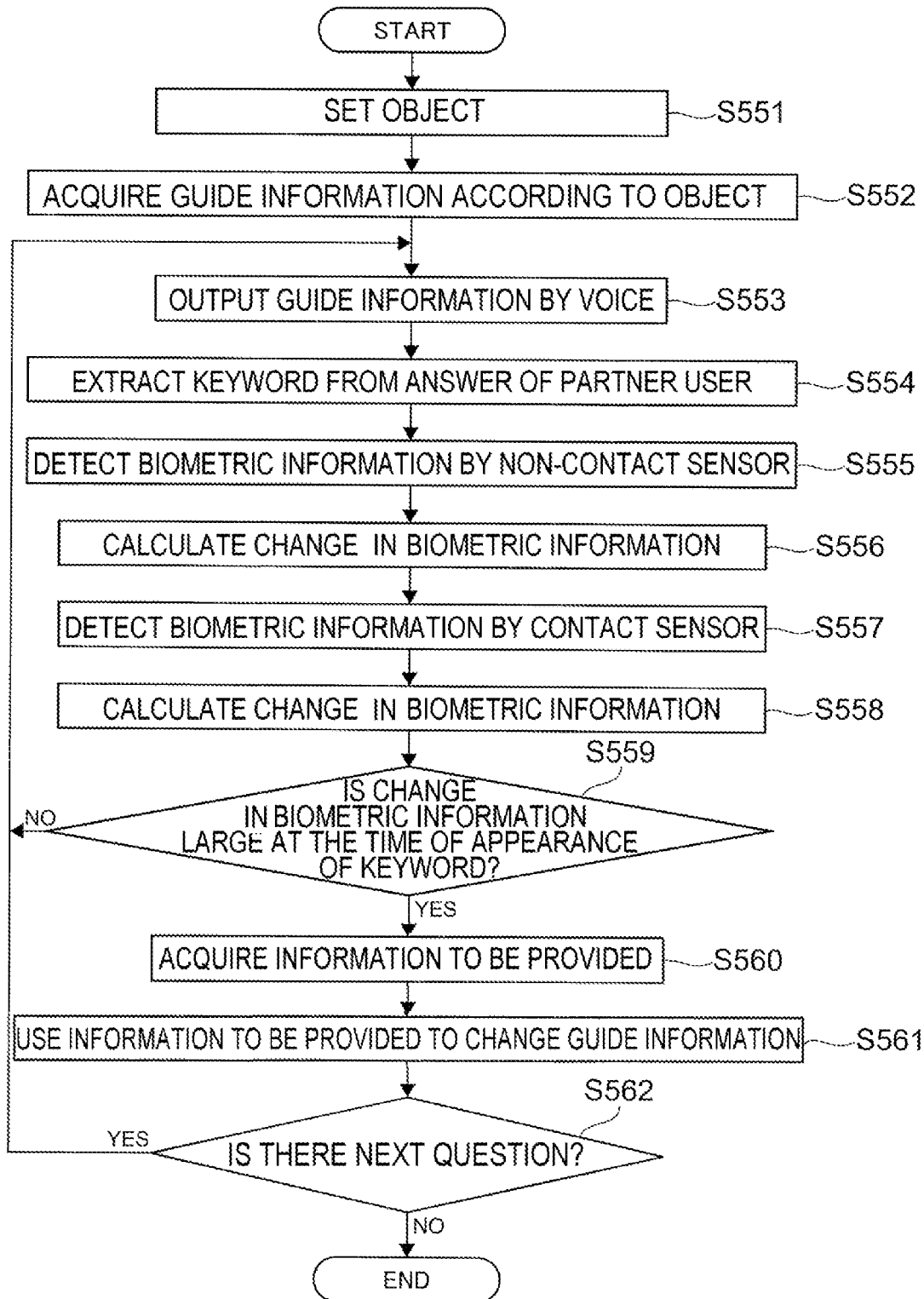
FIG. 16 is a flowchart illustrating an operation example of the information providing device according to the fifth exemplary embodiment of the invention in a second situation.

FIG. 16 is a flowchart illustrating an operation example of the information providing device 50 in the second situation in the fifth exemplary embodiment.

As illustrated, in the information providing device 50, first, the object setting unit 51 sets the object of providing information (step 551).

Then, the guide information acquisition unit 52 acquires the guide information according to the object set by the object setting unit 51 (step 552).

Next, the information output unit 57 outputs the guide information acquired in step 552 to the operating user by voice (step 553).

While listening to this guide information, when the operating user asks the partner user a question and the partner user answers the question, the interaction content analysis unit 55 extracts a keyword from the answer (step 554).

Meanwhile, the non-contact detection unit 53 uses the non-contact sensor to detect the biometric information of the partner user (step 555). Then, the non-contact detection unit 53 calculates a change in the detected biometric information (step 556).

Meanwhile, the contact detection unit 54 uses the contact sensor to detect the biometric information of the partner user (step 557). Then, the contact detection unit 54 calculates a change in the detected biometric information (step 558).

Then, the information acquisition unit 56 determines whether or not the change in the biometric information calculated in steps 556 and 558 is large at the time of appearance of the keyword extracted in step 554 (step 559). Specifically, the information acquisition unit 56 determines whether or not the change in the biometric information calculated in steps 556 and 558 is larger than a predetermined threshold value.

When it is determined that the change in the biometric information is large at the time of appearance of the keyword, the information acquisition unit 56 acquires information to be provided according to the keyword (step 560).

Next, the guide information controller 58 uses the information to be provided, which is acquired in step 560, to change the guide information acquired in step 552 (step 561).

Thereafter, the interaction content analysis unit 55 determines whether or not the next question is included in the guide information (step 562). Even when it is determined in step 559 that the change in the biometric information is not large at the time of appearance of the keyword, the interaction content analysis unit 55 determines whether or not the next question is included in the guide information (step 562). When it is determined that the next question is included in the guide information, the information providing device 50 returns the process to step 553 to repeat the subsequent steps. On the other hand, when it is determined that the next question is not included in the guide information, the information providing device 50 ends the process.

[Hardware Configuration of Information Providing Device]

The information providing devices 10 to 50 in the first to fifth exemplary embodiments may be implemented by a so-called hearable device which transmits information directly to the operating user's sense of hearing. This is because the hearable device has an advantage that it can gently transmit information to only the operating user without notifying the partner user of the information. Thus, a hearable device 90 may be used to implement the information providing devices 10 to 50, and the hardware configuration of the hearable device 90 will be described.

Figure 17:
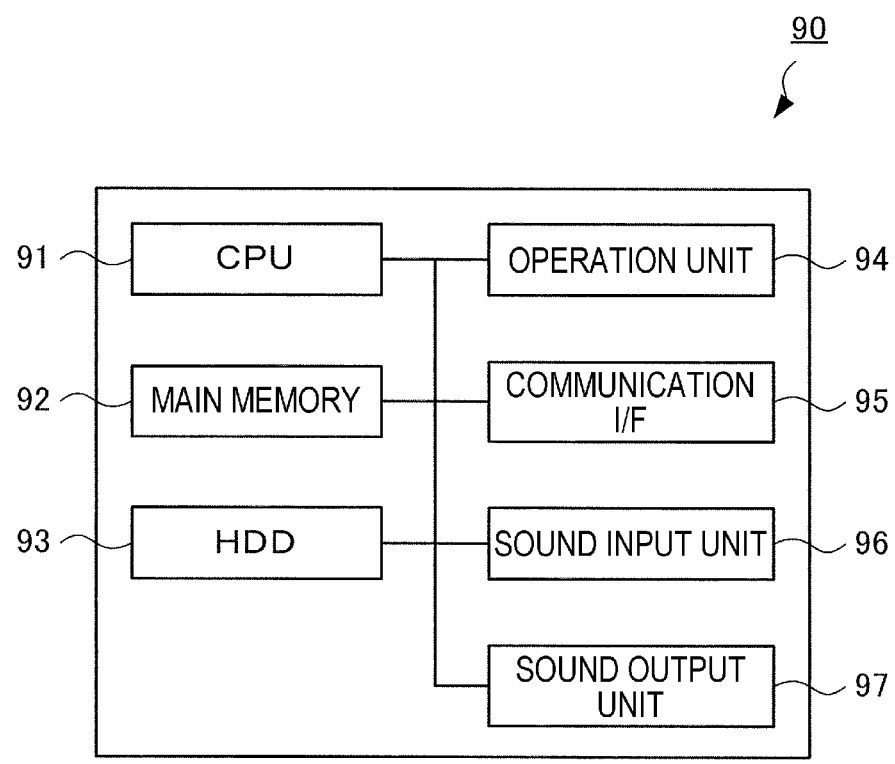
FIG. 17 is a view illustrating a hardware configuration example of the information providing devices according to the first to fifth exemplary embodiments of the invention.

FIG. 17 is a view illustrating a hardware configuration of the hearable device 90. As illustrated in the drawing, the hearable device 90 includes a CPU 91 which is an arithmetic unit, and a main memory 92 and a hard disk drive (HDD) 93 which are storage units. Here, the CPU 91 executes various kinds of software such as an operating system (OS) and applications to implement the respective processing units described above. Further, the main memory 92 stores various kinds of software and data for use in its execution, and the HDD 93 stores input data for various kinds of software, output data from various kinds of software, and the like. Furthermore, the hearable device 90 includes an operation unit 94 for the operating user to perform various operations, a communication interface (denoted as "communication I/F" in the drawing) 95 for performing communication with the outside, a sound input unit 96 to which a sound is input from a microphone or the like, and a sound output unit 97 for outputting a sound to an earphone, a headphone or the like. Incidentally, the earphone, the headphone or the like may be a bone conduction earphone, a bone conduction headphone or the like, which transmits sound by directly transferring the vibration of air to the skull.

Here, the hearable device 90 may be an earphone type or a headphone type device.

When the hearable device 90 is an earphone type device, the hearable device 90 is provided with an attachment unit that attaches this device to one ear of the operating user using the device. In this case, as in the second and fourth exemplary embodiments, when the information output units 27 and 47 output, by voice, the guide information and the information to be provided, the sound output unit 97 may transmit the guide information and the information to be provided to one of the left and right ears of the operating user while switching between the guide information and the information to be provided through the operation of the operation unit 94.

When the hearable device 90 is a headphone type device, the hearable device 90 is provided with an attachment unit that attaches this device to the operating user's head. In this case, as in the second and fourth exemplary embodiments, when the information output units 27 and 47 output, by voice, the guide information and the information to be provided, the sound output unit 97 may transmit the guide information and the information to be provided to one of the left and right ears of the operating user while switching between the guide information and the information to be provided through the operation of the operation unit 94 or may transmit the guide information to one of the left and right ears of the operating user and the information to be provided to the other of the left and right ears of the operating user without the operation of the operation unit 94.

Alternatively, the hearable device 90 may be a portable information terminal such as a smartphone, a tablet terminal or the like connected to an earphone, a headphone or the like. Also in this case, as in the second and fourth exemplary embodiments, when the information output units 27 and 47 output, by voice, the guide information and the information to be provided, the sound output unit 97 may transmit the guide information and the information to be provided to one of the left and right ears of the operating user while switching between the guide information and the information to be provided through the operation of the operation unit 94 or may transmit the guide information to one of the left and right ears of the operating user and the information to be provided to the other of the left and right ears of the operating user without the operation of the operation unit 94.

[Program]

The processes performed by the information providing devices 10 to 50 in the first to fifth exemplary embodiments are prepared, for example, as a program such as application software.

That is, the program that achieves the first to fifth exemplary embodiments is defined as a program that causes a computer to execute an information transmission process that includes: determining a situation of an interlocutor who interacts with a user; and transmitting, to the user, information to be provided according to the determined situation of the interlocutor.

The program implementing the exemplary embodiments can be provided not only by a communication unit but also stored in a recording medium such as a CD-ROM.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An information transmission device comprising:
a hardware processor configured to
determine a situation of an interlocutor who interacts with a user;
transmit, to the user, information to be provided according to the determined situation of the interlocutor;
specify an object of the situation of the interlocutor;
acquire a guide information that guides a series of questions according to the specified object of the interlocutor;
extract a keyword from an answer of the interlocutor when the user asks the interlocutor a question from the series of questions guided by the guide information;
detect a biometric information of the interlocutor; and
determine whether or not a change in the biometric information is greater than a predetermined threshold value in an appearance of the keyword extracted,
wherein the guide information is used as an instruction information that instructs a procedure for determining the situation of the interlocutor, and the object is set to be a specific category that includes a symptom of the interlocutor for consultation, a product for sales or a defect of a product for maintenance.

2. The information transmission device according to claim 1, wherein the hardware processor is configured to determine a situation related to a body of the interlocutor as the situation of the interlocutor.

3. The information transmission device according to claim 2, wherein the hardware processor is configured to determine a physical condition of the interlocutor or a change in the physical condition as the situation related to the body of the interlocutor.

4. The information transmission device according to claim 3, wherein the hardware processor is configured to determine the physical condition of the interlocutor or the change in the physical condition using a non-contact detector that detects the physical condition of the interlocutor without contacting with the body of the interlocutor.

5. The information transmission device according to claim 3, wherein the hardware processor is configured to determine the physical condition of the interlocutor or the change in the physical condition using a contact detector that detects the physical condition of the interlocutor while contacting with the body of the interlocutor.

6. The information transmission device according to claim 1, wherein the hardware processor is configured to determine a situation related to conversation of the interlocutor as the situation of the interlocutor.

7. The information transmission device according to claim 6, wherein the hardware processor is configured to determine contents of an answer of the interlocutor to a question of the user as the situation related to the conversation of the interlocutor.

8. The information transmission device according to claim 1, wherein the hardware processor is configured to determine, as the situation of the interlocutor, a situation related to a body of the interlocutor and a situation related to conversation of the interlocutor, and transmit, to the user, information to be provided according to the situation related to the body of the interlocutor and the situation related to the conversation of the interlocutor.

9. The information transmission device according to claim 8, wherein the hardware processor is configured to determine a physical condition of the interlocutor as the situation related to the body of the interlocutor and determine contents of an answer of the interlocutor to a question of the user as the situation related to the conversation of the interlocutor, and transmit, to the user, information to be provided according to the physical condition of the interlocutor and the contents of the answer of the interlocutor.

10. The information transmission device according to claim 9, wherein the hardware processor is configured to transmit, to the user, information to be provided in association with the physical condition of the interlocutor and the contents of the answer of the interlocutor with respect to the specified object.

11. The information transmission device according to claim 8, wherein the hardware processor is configured to determine a change in a physical condition of the interlocutor as the situation related to the body of the interlocutor and determine contents of an answer of the interlocutor to a question of the user as the situation related to the conversation of the interlocutor, and transmit, to the user, information to be provided according to the change in the physical condition of the interlocutor at the time of appearance of the contents of the answer of the interlocutor.

12. The information transmission device according to claim 1, wherein the hardware processor is configured to further transmit, to the user, the instruction information that instructs the procedure for determining the situation of the interlocutor.

13. The information transmission device according to claim 12, wherein the hardware processor is configured to transmit, to the user, the instruction information according to the specified object.

14. The information transmission device according to claim 12, wherein the hardware processor is configured to transmit, to the user, the instruction information changed based on the information to be provided.

15. The information transmission device according to claim 12, wherein the hardware processor is configured to transmit, to one of left and right ears of the user, the instruction information and the information to be provided while switching between the instruction information and the information to be provided through operation of an operation unit.

16. The information transmission device according to claim 12, wherein the hardware processor is configured to transmit the instruction information to one of left and right ears of the user and transmit the information to be provided to a remaining one of the left and right ears of the user.

17. The information transmission device according to claim 12, wherein the hardware processor is configured to transmit, to the user, the instruction information that instructs the procedure for questioning by the user and information to be provided according to contents of an answer of the interlocutor to a question of the user.

18. The information transmission device according to claim 17, wherein the hardware processor is configured that after starting transmission of a portion of the instruction information instructing a specific question to the user, the hardware processor does not transmit, to the user, information to be provided according to contents of an answer of the interlocutor to a question before the specific question.

19. The information transmission device according to claim 17, wherein the hardware processor is configured to after starting transmission of a portion of the instruction information instructing a specific question to the user and before ending transmission of all portions of the instruction information to the user, transmit, to the user, information to be provided according to contents of an answer of the interlocutor to a question before the specific question.

20. The information transmission device according to claim 17, wherein the hardware processor is configured to after ending transmission of all portions of the instruction information to the user, transmit, to the user, information to be provided according to contents of an answer of the interlocutor to a specific question in the instruction information.

21. A non-transitory computer readable medium storing a program causing a computer to execute an information transmission process, the information transmission process comprising:
   determining a situation of an interlocutor who interacts with a user;
   transmitting, to the user, information to be provided according to the determined situation of the interlocutor;
   specifying an object of the situation of the interlocutor;
   acquiring a guide information that guides a series of questions according to the specified object of the interlocutor;
   extracting a keyword from an answer of the interlocutor when the user asks the interlocutor a question from the series of questions guided by the guide information;

detecting a biometric information of the interlocutor; and
determining whether or not a change in the biometric information is greater than a predetermined threshold value in an appearance of the keyword extracted,
wherein the guide information is used as an instruction information that instructs a procedure for determining the situation of the interlocutor, and the object is set to be a specific category that includes a symptom of the interlocutor for consultation, a product for sales or a defect of a product for maintenance.

* * * * *